United States Patent
Snow et al.

(10) Patent No.: US 8,840,541 B2
(45) Date of Patent: Sep. 23, 2014

(54) PRESSURE SENSING GASTRIC BANDING SYSTEM

(75) Inventors: Sean Snow, Carpinteria, CA (US); Janel Birk, Oxnard, CA (US)

(73) Assignee: Apollo Endosurgery, Inc., Austin, TX (US)

( * ) Notice: Subject to any disclaimer, the term of this patent is extended or adjusted under 35 U.S.C. 154(b) by 692 days.

(21) Appl. No.: 12/712,833

(22) Filed: Feb. 25, 2010

(65) Prior Publication Data

US 2011/0208220 A1    Aug. 25, 2011

(51) Int. Cl.
| | |
|---|---|
| A61F 2/00 | (2006.01) |
| A61F 13/00 | (2006.01) |
| A61B 17/08 | (2006.01) |
| A61F 5/00 | (2006.01) |

(52) U.S. Cl.
CPC ...................... A61F 5/005 (2013.01)
USPC ............... 600/37; 600/488; 606/65; 606/157; 606/201; 606/202; 606/153; 604/65; 713/310

(58) Field of Classification Search
USPC ............ 600/37, 488; 606/201, 202, 153, 157; 604/65
See application file for complete search history.

(56) References Cited

U.S. PATENT DOCUMENTS

| | | |
|---|---|---|
| 1,174,814 A | 3/1916 | Brennan et al. |
| 1,830,947 A | 11/1931 | Klingel |
| 1,999,683 A | 4/1935 | Borresen |
| 2,163,048 A | 6/1939 | McKee |
| 2,339,138 A | 1/1944 | Black |
| 2,405,667 A | 8/1946 | Ottesen |
| 2,438,231 A | 3/1948 | Schultz et al. |
| 2,635,907 A | 4/1953 | Heimbuch |
| 2,714,469 A | 8/1955 | Carlson |
| 2,936,980 A | 5/1960 | Rapata |
| 3,059,645 A | 10/1962 | Hasbrouck et al. |
| 3,189,961 A | 6/1965 | Heller |
| 3,667,081 A | 6/1972 | Burger |
| 3,840,018 A | 10/1974 | Heifetz |

(Continued)

FOREIGN PATENT DOCUMENTS

| | | |
|---|---|---|
| CA | 949965 | 6/1974 |
| CN | 1250382 | 4/2000 |

(Continued)

OTHER PUBLICATIONS

Bio Enterics Lap-Band Adjustable Gastric Banding System, Inamed Health, pub. Aug. 28, 2003, pp. 1-115.

(Continued)

*Primary Examiner* — Christine Matthews
*Assistant Examiner* — Sunita Reddy
(74) *Attorney, Agent, or Firm* — Gordon & Jacobson, PC

(57) ABSTRACT

An implantable device monitors a pressure of fluid within an inflatable portion of a gastric band. The implantable device comprises a tube defining a lumen, and a pressure sensor positioned within at least one of the lumen or the tube. The pressure sensor is configured to sense the pressure of the fluid within the inflatable portion of the gastric band. The pressure sensor is also configured to transmit a pressure signal based on the pressure to a microcontroller, which transmits the pressure signal to a remote control device. The pressure sensor confers strain relief upon at least a portion of the tube, and the pressure sensor shields at least a portion of the tube from puncture by a needle.

15 Claims, 5 Drawing Sheets

(56) References Cited

U.S. PATENT DOCUMENTS

| | | | |
|---|---|---|---|
| 3,955,834 A | 5/1976 | Ahlrot | |
| 4,053,176 A | 10/1977 | Hilbush | |
| 4,117,727 A | 10/1978 | Friswell et al. | |
| 4,118,805 A | 10/1978 | Reimels | |
| 4,133,315 A | 1/1979 | Berman et al. | |
| 4,157,713 A | 6/1979 | Clarey | |
| 4,176,412 A | 12/1979 | Peterson | |
| 4,236,521 A | 12/1980 | Lauterjung | |
| 4,271,827 A | 6/1981 | Angelchick | |
| 4,286,584 A | 9/1981 | Sampson et al. | |
| 4,299,012 A | 11/1981 | Oetiker | |
| 4,340,083 A | 7/1982 | Cummins | |
| 4,370,982 A | 2/1983 | Reilly | |
| 4,399,809 A | 8/1983 | Baro et al. | |
| 4,406,656 A | 9/1983 | Hattler et al. | |
| 4,408,597 A | 10/1983 | Tenney, Jr. et al. | |
| 4,417,567 A | 11/1983 | Trick | |
| 4,424,208 A | 1/1984 | Wallace et al. | |
| 4,442,153 A | 4/1984 | Meltsch | |
| 4,450,375 A | 5/1984 | Siegal | |
| 4,485,805 A | 12/1984 | Foster, Jr. | |
| 4,492,004 A | 1/1985 | Oetiker | |
| 4,551,862 A | 11/1985 | Haber | |
| 4,558,699 A | 12/1985 | Bashour | |
| 4,559,699 A | 12/1985 | Owen et al. | |
| 4,582,640 A | 4/1986 | Smestad et al. | |
| 4,582,865 A | 4/1986 | Balazs et al. | |
| 4,592,339 A | 6/1986 | Kuzmak et al. | |
| 4,592,355 A | 6/1986 | Antebi | |
| 4,601,713 A | 7/1986 | Fuqua | |
| 4,603,699 A | 8/1986 | Himpens | |
| 4,628,928 A * | 12/1986 | Lowell | 606/1 |
| 4,667,672 A | 5/1987 | Romanoski | |
| 4,671,351 A | 6/1987 | Rappe | |
| 4,693,695 A | 9/1987 | Cheng | |
| 4,694,827 A | 9/1987 | Weiner et al. | |
| 4,696,288 A | 9/1987 | Kuzmak et al. | |
| 4,708,140 A | 11/1987 | Baron | |
| 4,716,154 A | 12/1987 | Malson et al. | |
| 4,753,086 A | 6/1988 | Schmidt | |
| 4,760,837 A | 8/1988 | Petit | |
| 4,803,075 A | 2/1989 | Wallace et al. | |
| 4,858,619 A | 8/1989 | Toth | |
| 4,872,483 A | 10/1989 | Shah | |
| 4,881,939 A | 11/1989 | Newman | |
| 4,883,467 A | 11/1989 | Franetzki et al. | |
| 4,886,787 A | 12/1989 | De Belder et al. | |
| 4,896,787 A | 1/1990 | Delamour et al. | |
| 4,915,690 A | 4/1990 | Cone et al. | |
| 4,919,650 A | 4/1990 | Feingold et al. | |
| 4,925,446 A | 5/1990 | Garay et al. | |
| 4,944,487 A | 7/1990 | Holtermann | |
| 4,944,659 A | 7/1990 | Labbe et al. | |
| 4,958,791 A | 9/1990 | Nakamura | |
| 4,969,899 A | 11/1990 | Cox, Jr. | |
| 4,989,756 A | 2/1991 | Kagamihara et al. | |
| 4,994,019 A | 2/1991 | Fernandez et al. | |
| 5,045,060 A | 9/1991 | Melsky et al. | |
| 5,074,868 A | 12/1991 | Kuzmak | |
| 5,084,061 A | 1/1992 | Gau et al. | |
| 5,091,171 A | 2/1992 | Yu et al. | |
| 5,116,652 A | 5/1992 | Alzner | |
| 5,120,313 A | 6/1992 | Elftman | 604/175 |
| 5,143,724 A | 9/1992 | Leshchiner et al. | |
| 5,152,770 A | 10/1992 | Bengmark et al. | |
| 5,156,157 A * | 10/1992 | Valenta et al. | 600/463 |
| 5,160,338 A | 11/1992 | Vincent | |
| 5,188,609 A | 2/1993 | Bayless et al. | |
| 5,224,494 A | 7/1993 | Enhorning | |
| 5,226,429 A | 7/1993 | Kuzmak | |
| 5,246,456 A | 9/1993 | Wilkinson | |
| 5,246,698 A | 9/1993 | Leshchiner et al. | |
| 5,259,399 A | 11/1993 | Brown | |
| 5,277,333 A | 1/1994 | Shimano | |
| 5,318,533 A | 6/1994 | Adams et al. | |
| 5,326,349 A | 7/1994 | Baraff | |
| 5,343,894 A | 9/1994 | Frisch et al. | |
| 5,356,883 A | 10/1994 | Kuo et al. | |
| 5,360,445 A | 11/1994 | Goldowsky | |
| 5,383,858 A | 1/1995 | Reilly et al. | |
| 5,391,156 A | 2/1995 | Hildwein et al. | |
| 5,399,351 A | 3/1995 | Leshchiner et al. | |
| 5,425,716 A | 6/1995 | Kawasaki et al. | |
| 5,449,363 A | 9/1995 | Brust et al. | |
| 5,449,368 A | 9/1995 | Kuzmak | |
| 5,458,568 A | 10/1995 | Racchini et al. | |
| 5,496,313 A | 3/1996 | Gentelia et al. | |
| 5,509,888 A | 4/1996 | Miller | |
| 5,531,716 A | 7/1996 | Luzio et al. | |
| 5,535,752 A | 7/1996 | Halperin et al. | 128/670 |
| 5,554,113 A | 9/1996 | Novak et al. | 604/30 |
| 5,562,714 A | 10/1996 | Grevious | |
| 5,569,839 A | 10/1996 | Ajot et al. | |
| 5,601,604 A | 2/1997 | Vincent | |
| 5,607,418 A | 3/1997 | Arzbaecher | |
| 5,633,001 A | 5/1997 | Agerup | |
| 5,649,546 A | 7/1997 | Steinbeck | |
| 5,653,718 A | 8/1997 | Yoon | |
| 5,658,298 A | 8/1997 | Vincent et al. | |
| 5,676,162 A | 10/1997 | Larson, Jr. et al. | |
| 5,681,284 A | 10/1997 | Herskowitz | |
| 5,695,504 A | 12/1997 | Gifford, III et al. | |
| 5,704,893 A | 1/1998 | Timm | |
| 5,713,911 A | 2/1998 | Racenet et al. | |
| 5,733,257 A | 3/1998 | Sternby | |
| 5,741,232 A | 4/1998 | Reilly et al. | |
| 5,748,200 A | 5/1998 | Funahashi | |
| 5,758,667 A | 6/1998 | Slettenmark | |
| 5,766,232 A | 6/1998 | Grevious et al. | |
| 5,769,877 A | 6/1998 | Barreras, Sr. | |
| 5,785,295 A | 7/1998 | Tsai | |
| 5,795,333 A | 8/1998 | Reilly et al. | |
| 5,807,311 A | 9/1998 | Palestrant | |
| 5,808,203 A | 9/1998 | Nolan, Jr. et al. | |
| 5,817,113 A | 10/1998 | Gifford, III et al. | |
| 5,827,529 A | 10/1998 | Ono et al. | |
| 5,833,698 A | 11/1998 | Hinchliffe et al. | |
| 5,861,014 A | 1/1999 | Familoni | |
| RE36,176 E | 3/1999 | Kuzmak | |
| 5,886,042 A | 3/1999 | Yu et al. | |
| 5,891,089 A | 4/1999 | Katz et al. | |
| 5,904,697 A | 5/1999 | Gifford, III et al. | |
| 5,910,149 A | 6/1999 | Kuzmak | |
| 5,928,195 A | 7/1999 | Malamud et al. | |
| 5,938,669 A | 8/1999 | Klaiber et al. | |
| 5,944,696 A | 8/1999 | Bayless et al. | |
| 5,944,751 A | 8/1999 | Laub | |
| 5,993,473 A | 11/1999 | Chan et al. | |
| 5,997,502 A | 12/1999 | Reilly et al. | |
| 6,010,511 A | 1/2000 | Murphy | |
| 6,013,679 A | 1/2000 | Kuo et al. | |
| 6,024,340 A | 2/2000 | Lazarus et al. | |
| 6,024,704 A | 2/2000 | Meador et al. | 600/486 |
| 6,048,309 A | 4/2000 | Flom et al. | |
| 6,067,991 A | 5/2000 | Forsell | |
| 6,074,341 A | 6/2000 | Anderson et al. | |
| 6,074,378 A | 6/2000 | Mouri et al. | |
| 6,083,249 A | 7/2000 | Familoni | |
| 6,090,064 A | 7/2000 | Reilly et al. | |
| 6,090,131 A | 7/2000 | Daley | |
| 6,102,678 A | 8/2000 | Peclat | |
| 6,102,922 A | 8/2000 | Jakobsson et al. | |
| 6,117,086 A | 9/2000 | Shulze | |
| 6,129,668 A | 10/2000 | Haynor et al. | |
| 6,171,321 B1 | 1/2001 | Gifford, III et al. | |
| 6,179,569 B1 | 1/2001 | Kojima et al. | |
| 6,193,734 B1 | 2/2001 | Bolduc et al. | |
| 6,203,523 B1 | 3/2001 | Haller et al. | |
| 6,210,345 B1 | 4/2001 | Van Brunt | |
| 6,210,347 B1 | 4/2001 | Forsell | |
| 6,221,024 B1 | 4/2001 | Miesel | 600/486 |
| 6,224,857 B1 | 5/2001 | Romeo et al. | |
| 6,306,088 B1 | 10/2001 | Krausman et al. | |
| 6,306,116 B1 | 10/2001 | Hancock | |

(56) References Cited

U.S. PATENT DOCUMENTS

| | | |
|---|---|---|
| 6,327,503 B1 | 12/2001 | Familoni |
| 6,371,942 B1 | 4/2002 | Schwartz et al. |
| 6,371,965 B2 | 4/2002 | Gifford, III et al. |
| 6,372,494 B1 | 4/2002 | Naughton et al. |
| 6,383,218 B1 | 5/2002 | Sourdile et al. |
| 6,383,219 B1 | 5/2002 | Telandro et al. |
| 6,387,105 B1 | 5/2002 | Gifford, III et al. |
| 6,402,717 B1 | 6/2002 | Reilly et al. |
| 6,402,718 B1 | 6/2002 | Reilly et al. |
| 6,417,750 B1 | 7/2002 | Shon |
| 6,418,934 B1 | 7/2002 | Chin |
| 6,419,696 B1 | 7/2002 | Ortiz et al. |
| 6,432,040 B1 | 8/2002 | Meah |
| 6,439,539 B1 | 8/2002 | Powell |
| 6,443,957 B1 | 9/2002 | Addis |
| 6,443,965 B1 | 9/2002 | Gifford, III et al. |
| 6,450,173 B1 | 9/2002 | Forsell |
| 6,450,946 B1 | 9/2002 | Forsell |
| 6,450,987 B1 | 9/2002 | Kramer |
| 6,451,034 B1 | 9/2002 | Gifford, III et al. |
| 6,453,907 B1 | 9/2002 | Forsell |
| 6,454,699 B1 | 9/2002 | Forsell |
| 6,454,700 B1 | 9/2002 | Forsell |
| 6,454,701 B1 | 9/2002 | Forsell |
| 6,454,785 B2 | 9/2002 | De Hoyos Garza |
| 6,457,801 B1 | 10/2002 | Fish et al. |
| 6,460,543 B1 | 10/2002 | Forsell |
| 6,461,293 B1 | 10/2002 | Forsell |
| 6,463,935 B1 | 10/2002 | Forsell |
| 6,464,628 B1 | 10/2002 | Forsell |
| 6,470,892 B1 | 10/2002 | Forsell |
| 6,474,584 B2 | 11/2002 | Ekich |
| 6,475,136 B1 | 11/2002 | Forsell |
| 6,475,192 B1 | 11/2002 | Reilly et al. |
| 6,485,496 B1 | 11/2002 | Suyker et al. |
| 6,491,704 B2 | 12/2002 | Gifford, III et al. |
| 6,491,705 B2 | 12/2002 | Gifford, III et al. |
| 6,511,490 B2 | 1/2003 | Robert |
| 6,517,556 B1 | 2/2003 | Monassevitch |
| 6,527,701 B1 | 3/2003 | Sayet et al. |
| 6,547,801 B1 | 4/2003 | Dargent et al. |
| 6,562,008 B1 | 5/2003 | Reilly et al. |
| 6,565,582 B2 | 5/2003 | Gifford, III et al. |
| 6,579,301 B1 | 6/2003 | Bales et al. |
| 6,601,604 B1 | 8/2003 | Cooper |
| 6,615,084 B1 | 9/2003 | Cigaina |
| 6,627,620 B1 | 9/2003 | Nielson |
| 6,630,486 B1 | 10/2003 | Royer |
| 6,632,239 B2 | 10/2003 | Snyder et al. |
| 6,635,020 B2 | 10/2003 | Tripp, Jr. et al. |
| 6,638,258 B2 | 10/2003 | Schwartz et al. |
| 6,646,628 B2 | 11/2003 | Shirochi et al. |
| 6,676,674 B1 | 1/2004 | Dudai |
| 6,685,668 B1 | 2/2004 | Cho et al. |
| 6,685,963 B1 | 2/2004 | Taupin et al. |
| 6,691,047 B1 | 2/2004 | Fredricks |
| 6,715,731 B1 | 4/2004 | Post et al. |
| 6,725,726 B1 | 4/2004 | Adolfs et al. |
| 6,729,600 B2 | 5/2004 | Mattes et al. |
| 6,733,478 B2 | 5/2004 | Reilly et al. |
| 6,754,527 B2 | 6/2004 | Stroebel et al. |
| 6,767,924 B2 | 7/2004 | Yu et al. |
| 6,778,927 B2 | 8/2004 | Cha et al. |
| 6,799,698 B2 | 10/2004 | Ono et al. |
| 6,808,513 B2 | 10/2004 | Reilly et al. |
| 6,811,136 B2 | 11/2004 | Eberhardt et al. |
| 6,820,651 B2 | 11/2004 | Seuret et al. |
| 6,824,554 B1 * | 11/2004 | Jang ............... 606/194 |
| 6,834,201 B2 | 12/2004 | Gillies et al. |
| 6,871,090 B1 | 3/2005 | He et al. |
| 6,889,086 B2 | 5/2005 | Mass et al. |
| 6,916,326 B2 | 7/2005 | Benchetrit |
| 6,921,819 B2 | 7/2005 | Piron et al. |
| 6,924,273 B2 | 8/2005 | Pirece |
| 6,940,467 B2 | 9/2005 | Fisher et al. |
| 6,966,875 B1 | 11/2005 | Longobardi |
| 7,017,583 B2 | 3/2006 | Forsell |
| 7,021,147 B1 | 4/2006 | Subramian ............... 73/708 |
| 7,027,935 B2 | 4/2006 | Shimase et al. |
| 7,037,344 B2 | 5/2006 | Kagan et al. |
| 7,040,349 B2 | 5/2006 | Moler et al. |
| 7,044,933 B2 | 5/2006 | VanDiver et al. |
| 7,054,690 B2 | 5/2006 | Imran |
| 7,058,434 B2 | 6/2006 | Wang et al. |
| 7,060,080 B2 | 6/2006 | Bachmann |
| 7,066,486 B2 | 6/2006 | Birk |
| 7,118,526 B2 | 10/2006 | Egle |
| 7,119,062 B1 | 10/2006 | Alvis et al. |
| 7,128,750 B1 | 10/2006 | Stergiopulos |
| 7,144,400 B2 | 12/2006 | Byrum et al. |
| 7,172,607 B2 | 2/2007 | Hofle et al. |
| 7,177,693 B2 | 2/2007 | Starkebsum |
| 7,191,007 B2 | 3/2007 | Desai et al. |
| 7,195,610 B1 | 3/2007 | Flachbart |
| 7,204,821 B1 | 4/2007 | Clare et al. |
| 7,223,239 B2 | 5/2007 | Schulze et al. |
| 7,238,191 B2 | 7/2007 | Bachmann |
| 7,240,607 B2 | 7/2007 | Fish |
| 7,255,675 B2 | 8/2007 | Gertner et al. |
| 7,263,405 B2 | 8/2007 | Boveja et al. |
| 7,282,023 B2 | 10/2007 | Frering |
| 7,288,064 B2 | 10/2007 | Boustani et al. |
| 7,297,103 B2 | 11/2007 | Jarsaillon et al. |
| 7,299,082 B2 | 11/2007 | Feldman et al. |
| 7,310,557 B2 | 12/2007 | Maschino et al. |
| 7,311,716 B2 | 12/2007 | Byrum |
| 7,311,717 B2 | 12/2007 | Egle |
| 7,314,443 B2 | 1/2008 | Jordan et al. |
| 7,314,598 B2 | 1/2008 | Nishino |
| 7,314,636 B2 | 1/2008 | Caseres et al. |
| 7,338,433 B2 | 3/2008 | Coe |
| 7,340,306 B2 | 3/2008 | Barrett et al. |
| 7,351,198 B2 | 4/2008 | Byrum et al. |
| 7,351,240 B2 | 4/2008 | Hassler, Jr. et al. |
| 7,364,542 B2 | 4/2008 | Jambor et al. |
| 7,367,340 B2 | 5/2008 | Nelson et al. |
| 7,367,937 B2 | 5/2008 | Jambor et al. |
| 7,374,565 B2 | 5/2008 | Hassler, Jr. et al. |
| 7,390,294 B2 | 6/2008 | Hassler, Jr. |
| 7,396,353 B2 | 7/2008 | Lorenzen et al. |
| 7,416,528 B2 | 8/2008 | Crawford et al. |
| 7,457,668 B2 | 11/2008 | Cancel et al. |
| 7,481,763 B2 | 1/2009 | Hassler, Jr. et al. |
| 7,500,944 B2 | 3/2009 | Byrum et al. |
| 7,502,649 B2 | 3/2009 | Ben-Haim et al. |
| 7,507,221 B2 | 3/2009 | Neer |
| 7,530,943 B2 | 5/2009 | Lechner |
| 7,585,280 B2 | 9/2009 | Wilson et al. |
| 7,594,885 B2 | 9/2009 | Byrum |
| 7,599,743 B2 | 10/2009 | Hassler, Jr. et al. |
| 7,599,744 B2 | 10/2009 | Giordano et al. |
| 7,601,162 B2 | 10/2009 | Hassle, Jr. et al. |
| 7,615,001 B2 | 11/2009 | Jambor et al. |
| 7,618,365 B2 | 11/2009 | Jambor et al. |
| 7,658,196 B2 | 2/2010 | Ferreri et al. |
| 7,670,279 B2 | 3/2010 | Gertner |
| 7,699,770 B2 | 4/2010 | Hassler, Jr. et al. |
| 7,712,470 B2 | 5/2010 | Gertner |
| 7,727,141 B2 | 6/2010 | Hassler, Jr. et al. |
| 7,741,476 B2 | 6/2010 | Lebreton |
| 7,758,493 B2 | 7/2010 | Gingras |
| 7,763,039 B2 | 7/2010 | Ortiz et al. |
| 7,766,815 B2 | 8/2010 | Ortiz |
| 7,771,439 B2 | 8/2010 | Griffiths |
| 7,775,215 B2 | 8/2010 | Hassler, Jr. et al. |
| 7,775,966 B2 | 8/2010 | Dlugos et al. |
| 7,775,967 B2 | 8/2010 | Gertner |
| 7,794,386 B2 | 9/2010 | Brooks |
| 7,811,298 B2 | 10/2010 | Birk |
| 7,824,422 B2 | 11/2010 | Benchetrit |
| 7,828,813 B2 | 11/2010 | Mouton |
| 7,832,407 B2 | 11/2010 | Gertner |
| 7,841,978 B2 | 11/2010 | Gertner |
| 7,844,342 B2 | 11/2010 | Dlugos, Jr. et al. |

(56) References Cited

U.S. PATENT DOCUMENTS

| | | |
|---|---|---|
| 7,862,502 B2 | 1/2011 | Pool et al. |
| 7,879,068 B2 | 2/2011 | Dlugos et al. |
| 7,927,270 B2 | 4/2011 | Dlugos et al. |
| 7,951,067 B2 | 5/2011 | Byrum et al. |
| 2001/0011543 A1 | 8/2001 | Forsell |
| 2002/0038105 A1 | 3/2002 | Schwartz et al. |
| 2002/0072780 A1 | 6/2002 | Foley |
| 2002/0091395 A1 | 7/2002 | Gabbay |
| 2002/0095181 A1 | 7/2002 | Beyar |
| 2002/0098097 A1 | 7/2002 | Singh |
| 2002/0123716 A1 | 9/2002 | VanDiver et al. |
| 2002/0133081 A1 | 9/2002 | Ackerman et al. |
| 2002/0139208 A1 | 10/2002 | Yatskov |
| 2002/0152816 A1 | 10/2002 | Kim |
| 2002/0177811 A1 | 11/2002 | Reilly et al. |
| 2002/0183765 A1 | 12/2002 | Adams |
| 2002/0193679 A1 | 12/2002 | Malave et al. |
| 2002/0198548 A1 | 12/2002 | Robert |
| 2003/0009123 A1 | 1/2003 | Brugger |
| 2003/0014003 A1 | 1/2003 | Gertner |
| 2003/0019498 A1 | 1/2003 | Forsell |
| 2003/0045775 A1 | 3/2003 | Forsell |
| 2003/0045902 A1 | 3/2003 | Weadock |
| 2003/0060754 A1 | 3/2003 | Reilly et al. |
| 2003/0060873 A1 | 3/2003 | Gertner et al. |
| 2003/0066536 A1 | 4/2003 | Forsell |
| 2003/0073880 A1 | 4/2003 | Polsky et al. |
| 2003/0093157 A1 | 5/2003 | Caseres et al. |
| 2003/0100910 A1 | 5/2003 | Gifford, III et al. |
| 2003/0120288 A1 | 6/2003 | Benchetrit |
| 2003/0148995 A1 | 8/2003 | Piron et al. |
| 2003/0158564 A1 | 8/2003 | Benchetrit |
| 2003/0158569 A1 | 8/2003 | Wazne |
| 2003/0167022 A1 | 9/2003 | Dijkman |
| 2003/0171887 A1 | 9/2003 | Cha et al. |
| 2003/0181890 A1 | 9/2003 | Schulze et al. |
| 2003/0181917 A1 | 9/2003 | Gertner |
| 2003/0191433 A1 | 10/2003 | Prentiss |
| 2003/0208212 A1 | 11/2003 | Cigaina |
| 2003/0213285 A1 | 11/2003 | Wheeler et al. |
| 2004/0000843 A1 | 1/2004 | East |
| 2004/0034479 A1 | 2/2004 | Shimase et al. |
| 2004/0044332 A1 | 3/2004 | Stergiopulos |
| 2004/0049209 A1 | 3/2004 | Benchetrit |
| 2004/0059393 A1 | 3/2004 | Policker et al. |
| 2004/0068847 A1 | 4/2004 | Belisle et al. |
| 2004/0069714 A1 | 4/2004 | Ferguson |
| 2004/0106899 A1 | 6/2004 | McMichael et al. |
| 2004/0133219 A1 | 7/2004 | Forsell |
| 2004/0147816 A1 | 7/2004 | Policker et al. |
| 2004/0148034 A1 | 7/2004 | Kagan et al. |
| 2004/0153106 A1 | 8/2004 | Dudai |
| 2004/0162595 A1 | 8/2004 | Foley |
| 2004/0171942 A1 | 9/2004 | Ackerman et al. |
| 2004/0215159 A1 | 10/2004 | Forsell |
| 2004/0230137 A1 | 11/2004 | Mouton |
| 2004/0235025 A1 | 11/2004 | Mori et al. |
| 2004/0243057 A1 | 12/2004 | Vinten-Johansen |
| 2004/0254533 A1 | 12/2004 | Schriver et al. |
| 2004/0254536 A1 | 12/2004 | Conlon et al. |
| 2004/0254537 A1 | 12/2004 | Conlon et al. |
| 2004/0260319 A1 | 12/2004 | Egle |
| 2004/0267288 A1 | 12/2004 | Byrum et al. |
| 2004/0267291 A1 | 12/2004 | Byrum et al. |
| 2004/0267292 A1 | 12/2004 | Byrum et al. |
| 2004/0267293 A1 | 12/2004 | Byrum et al. |
| 2004/0267377 A1 | 12/2004 | Egle |
| 2005/0002984 A1 | 1/2005 | Byrum et al. |
| 2005/0038484 A1 | 2/2005 | Knudson et al. |
| 2005/0038498 A1 | 2/2005 | Dubrow et al. |
| 2005/0055039 A1 | 3/2005 | Burnett et al. |
| 2005/0070934 A1 | 3/2005 | Tanaka et al. |
| 2005/0070937 A1 | 3/2005 | Jambor et al. |
| 2005/0100779 A1 | 5/2005 | Gertner |
| 2005/0104457 A1 | 5/2005 | Jordan et al. |
| 2005/0119672 A1 | 6/2005 | Benchetrit |
| 2005/0119674 A1 | 6/2005 | Gingras |
| 2005/0122580 A1 | 6/2005 | Birk |
| 2005/0131383 A1 | 6/2005 | Chen et al. |
| 2005/0131485 A1 | 6/2005 | Knudson et al. |
| 2005/0136122 A1 | 6/2005 | Sadozai et al. |
| 2005/0142152 A1 | 6/2005 | Leshchiner et al. |
| 2005/0143765 A1 | 6/2005 | Bachmann et al. |
| 2005/0143766 A1 | 6/2005 | Bachmann et al. |
| 2005/0154274 A1 | 7/2005 | Jarsaillon et al. |
| 2005/0171568 A1 | 8/2005 | Duffy |
| 2005/0177111 A1 | 8/2005 | Ozeri et al. |
| 2005/0183730 A1 | 8/2005 | Byrum |
| 2005/0192531 A1 | 9/2005 | Birk |
| 2005/0192601 A1 | 9/2005 | Demarais |
| 2005/0192614 A1 | 9/2005 | Binmoeller |
| 2005/0192629 A1 | 9/2005 | Saadat et al. |
| 2005/0216042 A1 | 9/2005 | Gertner |
| 2005/0226936 A1 | 10/2005 | Agerup |
| 2005/0228415 A1 | 10/2005 | Gertner |
| 2005/0228504 A1 | 10/2005 | Demarais |
| 2005/0240155 A1 | 10/2005 | Conlon |
| 2005/0240156 A1 | 10/2005 | Conlon |
| 2005/0240279 A1 | 10/2005 | Kagan et al. |
| 2005/0244288 A1 | 11/2005 | O'Neil |
| 2005/0250979 A1 | 11/2005 | Coe |
| 2005/0251181 A1 | 11/2005 | Bachmann |
| 2005/0251182 A1 | 11/2005 | Bachmann |
| 2005/0267406 A1 | 12/2005 | Hassler, Jr. |
| 2005/0267500 A1 | 12/2005 | Hassler, Jr. |
| 2005/0267533 A1 | 12/2005 | Gertner |
| 2005/0271729 A1 | 12/2005 | Wang |
| 2005/0277899 A1 | 12/2005 | Conlon et al. |
| 2005/0283041 A1 | 12/2005 | Egle |
| 2005/0288739 A1 | 12/2005 | Hassler, Jr. et al. |
| 2005/0288740 A1 | 12/2005 | Hassler, Jr. et al. |
| 2006/0009697 A1 | 1/2006 | Banet et al. |
| 2006/0015138 A1 | 1/2006 | Gertner |
| 2006/0020239 A1* | 1/2006 | Geiger et al. ............ 604/9 |
| 2006/0020298 A1 | 1/2006 | Camilleri et al. |
| 2006/0041183 A1 | 2/2006 | Massen et al. |
| 2006/0074439 A1 | 4/2006 | Garner et al. |
| 2006/0074473 A1 | 4/2006 | Gertner |
| 2006/0079766 A1 | 4/2006 | Neer et al. |
| 2006/0079767 A1 | 4/2006 | Gibbs et al. |
| 2006/0089571 A1 | 4/2006 | Gertner |
| 2006/0122147 A1 | 6/2006 | Wohlrab |
| 2006/0142700 A1 | 6/2006 | Sobelman et al. |
| 2006/0142790 A1 | 6/2006 | Gertner |
| 2006/0149161 A1 | 7/2006 | Wilson et al. |
| 2006/0161139 A1 | 7/2006 | Levine et al. |
| 2006/0161186 A1 | 7/2006 | Hassler, Jr. et al. |
| 2006/0167531 A1 | 7/2006 | Gertner et al. |
| 2006/0173238 A1 | 8/2006 | Starkebaum |
| 2006/0173424 A1 | 8/2006 | Conlon |
| 2006/0183967 A1 | 8/2006 | Lechner |
| 2006/0189887 A1 | 8/2006 | Hassler, Jr. et al. |
| 2006/0189888 A1 | 8/2006 | Hassler et al. ............ 600/37 |
| 2006/0189889 A1 | 8/2006 | Gertner |
| 2006/0194758 A1 | 8/2006 | Lebreton |
| 2006/0195139 A1 | 8/2006 | Gertner |
| 2006/0197412 A1 | 9/2006 | Rasmussen |
| 2006/0199997 A1 | 9/2006 | Hassler, Jr. et al. |
| 2006/0211912 A1 | 9/2006 | Dlugos et al. |
| 2006/0211913 A1 | 9/2006 | Dlugos et al. |
| 2006/0211914 A1 | 9/2006 | Hassler, Jr. et al. |
| 2006/0212051 A1 | 9/2006 | Snyder et al. |
| 2006/0212053 A1 | 9/2006 | Gertner |
| 2006/0235448 A1 | 10/2006 | Roslin et al. |
| 2006/0246137 A1 | 11/2006 | Hermitte et al. |
| 2006/0247721 A1 | 11/2006 | Maschino et al. |
| 2006/0247722 A1 | 11/2006 | Maschino et al. |
| 2006/0247724 A1 | 11/2006 | Gerber et al. |
| 2006/0252982 A1 | 11/2006 | Hassler, Jr. |
| 2006/0252983 A1 | 11/2006 | Lembo et al. |
| 2006/0257488 A1 | 11/2006 | Hubbard |
| 2006/0264699 A1 | 11/2006 | Gertner |
| 2006/0264762 A1 | 11/2006 | Starr |
| 2006/0276812 A1 | 12/2006 | Hill et al. |

(56) References Cited

U.S. PATENT DOCUMENTS

| | | |
|---|---|---|
| 2006/0293627 A1 | 12/2006 | Byrum et al. |
| 2007/0001447 A1 | 1/2007 | Fennington, Jr. |
| 2007/0015954 A1 | 1/2007 | Dlugos |
| 2007/0015955 A1 | 1/2007 | Tsonton |
| 2007/0015956 A1 | 1/2007 | Crawford et al. |
| 2007/0016231 A1 | 1/2007 | Jambor et al. |
| 2007/0016262 A1 | 1/2007 | Gross et al. |
| 2007/0027356 A1 | 2/2007 | Ortiz |
| 2007/0027358 A1 | 2/2007 | Gertner et al. |
| 2007/0044655 A1 | 3/2007 | Fish |
| 2007/0077292 A1 | 4/2007 | Pinsky |
| 2007/0078476 A1 | 4/2007 | Hull, Sr. et al. |
| 2007/0106153 A1 | 5/2007 | Neer et al. |
| 2007/0125826 A1 | 6/2007 | Shelton |
| 2007/0156013 A1 | 7/2007 | Birk ................... 600/37 |
| 2007/0167672 A1 | 7/2007 | Dlugos et al. |
| 2007/0167982 A1 | 7/2007 | Gertner et al. |
| 2007/0173685 A1 | 7/2007 | Jambor et al. |
| 2007/0173888 A1 | 7/2007 | Gertner et al. |
| 2007/0179335 A1 | 8/2007 | Gertner et al. |
| 2007/0185373 A1 | 8/2007 | Tsonton |
| 2007/0185462 A1 | 8/2007 | Byrum |
| 2007/0191717 A1 | 8/2007 | Rosen et al. |
| 2007/0213836 A1 | 9/2007 | Paganon |
| 2007/0218083 A1 | 9/2007 | Brooks |
| 2007/0232848 A1 | 10/2007 | Forsell |
| 2007/0232849 A1 | 10/2007 | Gertner |
| 2007/0233170 A1 | 10/2007 | Gertner |
| 2007/0235083 A1 | 10/2007 | Dlugos et al. |
| 2007/0243227 A1 | 10/2007 | Gertner |
| 2007/0250085 A1 | 10/2007 | Bachmann et al. |
| 2007/0250086 A1 | 10/2007 | Wiley et al. |
| 2007/0255335 A1 | 11/2007 | Herbert et al. |
| 2007/0255336 A1 | 11/2007 | Herbert et al. |
| 2007/0265598 A1 | 11/2007 | Karasik |
| 2007/0265645 A1 | 11/2007 | Birk et al. |
| 2007/0265646 A1 | 11/2007 | McCoy et al. |
| 2007/0293716 A1 | 12/2007 | Baker et al. |
| 2007/0298005 A1 | 12/2007 | Thibault |
| 2008/0009680 A1 | 1/2008 | Hassler, Jr. |
| 2008/0015406 A1 | 1/2008 | Dlugos et al. |
| 2008/0015501 A1 | 1/2008 | Gertner |
| 2008/0027269 A1 | 1/2008 | Gertner |
| 2008/0027469 A1 | 1/2008 | Bachmann |
| 2008/0071306 A1 | 3/2008 | Gertner |
| 2008/0097496 A1 | 4/2008 | Chang et al. |
| 2008/0108862 A1 | 5/2008 | Jordan et al. |
| 2008/0108896 A1 | 5/2008 | Gibb et al. |
| 2008/0108941 A1 | 5/2008 | Neer |
| 2008/0108943 A1 | 5/2008 | Wagner |
| 2008/0114302 A1 | 5/2008 | Neer |
| 2008/0147002 A1 | 6/2008 | Gertner |
| 2008/0161717 A1* | 7/2008 | Gertner .................. 600/561 |
| 2008/0161875 A1 | 7/2008 | Stone |
| 2008/0166028 A1 | 7/2008 | Turek et al. |
| 2008/0167647 A1 | 7/2008 | Gertner |
| 2008/0167648 A1 | 7/2008 | Gertner |
| 2008/0172072 A1 | 7/2008 | Pool et al. |
| 2008/0188766 A1 | 8/2008 | Gertner |
| 2008/0195092 A1 | 8/2008 | Kim et al. |
| 2008/0208240 A1 | 8/2008 | Paz |
| 2008/0221598 A1* | 9/2008 | Dlugos et al. .......... 606/157 |
| 2008/0243071 A1 | 10/2008 | Quijano et al. |
| 2008/0249806 A1 | 10/2008 | Dlugos et al. |
| 2008/0250340 A1 | 10/2008 | Dlugos et al. |
| 2008/0250341 A1 | 10/2008 | Dlugos et al. |
| 2008/0255403 A1 | 10/2008 | Voegele et al. |
| 2008/0255414 A1 | 10/2008 | Voegele et al. |
| 2008/0255425 A1 | 10/2008 | Voegele et al. |
| 2008/0255459 A1 | 10/2008 | Voegele et al. |
| 2008/0255537 A1 | 10/2008 | Voegele et al. |
| 2008/0275294 A1 | 11/2008 | Gertner |
| 2008/0275295 A1 | 11/2008 | Gertner |
| 2008/0275484 A1 | 11/2008 | Gertner |
| 2008/0281347 A1 | 11/2008 | Gertner |
| 2008/0287969 A1 | 11/2008 | Tsonton et al. |
| 2008/0287974 A1 | 11/2008 | Widenhouse et al. |
| 2008/0287976 A1 | 11/2008 | Weaner et al. |
| 2008/0294097 A1 | 11/2008 | Kim et al. |
| 2008/0300618 A1 | 12/2008 | Gertner |
| 2008/0306443 A1 | 12/2008 | Neer et al. |
| 2008/0319435 A1 | 12/2008 | Rioux et al. |
| 2009/0054914 A1 | 2/2009 | Lechner |
| 2009/0062825 A1 | 3/2009 | Pool et al. |
| 2009/0062826 A1 | 3/2009 | Steffen |
| 2009/0082793 A1 | 3/2009 | Birk |
| 2009/0118572 A1 | 5/2009 | Lechner |
| 2009/0149874 A1 | 6/2009 | Ortiz et al. |
| 2009/0157106 A1 | 6/2009 | Marcotte et al. |
| 2009/0157107 A1 | 6/2009 | Kierath et al. |
| 2009/0157113 A1 | 6/2009 | Marcotte et al. |
| 2009/0163803 A1 | 6/2009 | Neer et al. |
| 2009/0171375 A1 | 7/2009 | Coe et al. |
| 2009/0171378 A1 | 7/2009 | Coe et al. |
| 2009/0171379 A1 | 7/2009 | Coe et al. |
| 2009/0187202 A1 | 7/2009 | Ortiz et al. |
| 2009/0188494 A1 | 7/2009 | Imai et al. |
| 2009/0192404 A1 | 7/2009 | Ortiz et al. |
| 2009/0192415 A1 | 7/2009 | Ortiz et al. |
| 2009/0192533 A1 | 7/2009 | Dlugos, Jr. et al. |
| 2009/0192534 A1 | 7/2009 | Ortiz et al. |
| 2009/0192541 A1 | 7/2009 | Ortiz et al. |
| 2009/0198261 A1 | 8/2009 | Schweikert |
| 2009/0202387 A1 | 8/2009 | Dlugos, Jr. et al. |
| 2009/0204131 A1 | 8/2009 | Ortiz et al. |
| 2009/0204132 A1 | 8/2009 | Ortiz et al. |
| 2009/0209995 A1 | 8/2009 | Byrum et al. |
| 2009/0216193 A1 | 8/2009 | Schriver et al. |
| 2009/0216255 A1 | 8/2009 | Coe et al. |
| 2009/0220176 A1 | 9/2009 | Fusco |
| 2009/0222031 A1 | 9/2009 | Axelsson |
| 2009/0222065 A1 | 9/2009 | Dlugos, Jr. et al. |
| 2009/0228063 A1 | 9/2009 | Dlugos, Jr. et al. |
| 2009/0228072 A1 | 9/2009 | Coe et al. |
| 2009/0241677 A1 | 10/2009 | Klees et al. |
| 2009/0270759 A1 | 10/2009 | Wilson et al. |
| 2009/0270904 A1 | 10/2009 | Birk ................... 606/192 |
| 2009/0306462 A1 | 12/2009 | Lechner |
| 2009/0312635 A1 | 12/2009 | Shimchuk et al. |
| 2009/0312785 A1* | 12/2009 | Stone et al. ............. 606/191 |
| 2010/0010291 A1 | 1/2010 | Birk et al. |
| 2010/0010327 A1* | 1/2010 | Merz et al. ............. 600/345 |
| 2010/0049224 A1 | 2/2010 | Vargas |
| 2010/0087843 A1 | 4/2010 | Bertolote et al. |
| 2010/0099945 A1 | 4/2010 | Birk et al. |
| 2010/0100079 A1 | 4/2010 | Berkcan |
| 2010/0145378 A1 | 6/2010 | Gertner |
| 2010/0152532 A1 | 6/2010 | Marcotte |
| 2010/0168508 A1 | 7/2010 | Gertner |
| 2010/0185049 A1 | 7/2010 | Birk et al. |
| 2010/0191265 A1 | 7/2010 | Lau et al. |
| 2010/0191271 A1 | 7/2010 | Lau et al. |
| 2010/0204647 A1 | 8/2010 | Gertner |
| 2010/0204723 A1 | 8/2010 | Gertner |
| 2010/0217071 A1 | 8/2010 | Ricol |
| 2010/0226988 A1 | 9/2010 | Lebreton |
| 2010/0228080 A1 | 9/2010 | Tavori et al. |
| 2010/0234682 A1 | 9/2010 | Gertner |
| 2010/0249803 A1 | 9/2010 | Griffiths |
| 2010/0280310 A1 | 11/2010 | Raven |
| 2010/0305397 A1 | 12/2010 | Birk et al. |
| 2010/0312046 A1 | 12/2010 | Lau et al. |
| 2010/0312147 A1 | 12/2010 | Gertner |
| 2010/0317978 A1* | 12/2010 | Maile et al. ............. 600/488 |
| 2010/0324358 A1 | 12/2010 | Birk et al. |
| 2010/0324359 A1 | 12/2010 | Birk et al. |
| 2011/0130626 A1 | 6/2011 | Hassler, Jr. et al. |
| 2011/0201874 A1 | 8/2011 | Birk et al. |

FOREIGN PATENT DOCUMENTS

| | | |
|---|---|---|
| CN | 1367670 | 9/2002 |
| DE | 4225524 | 2/1994 |
| DE | 19802615 | 8/1999 |

(56) References Cited

FOREIGN PATENT DOCUMENTS

| | | |
|---|---|---|
| DE | 10020688 | 12/2000 |
| EP | 0119596 | 9/1984 |
| EP | 0230747 | 8/1987 |
| EP | 0416250 | 3/1991 |
| EP | 0611561 | 8/1994 |
| EP | 0695558 | 2/1996 |
| EP | 0876808 | 11/1998 |
| EP | 1036545 | 9/2000 |
| EP | 1072282 | 1/2001 |
| EP | 1105073 | 6/2001 |
| EP | 1396242 | 3/2004 |
| EP | 1396243 | 3/2004 |
| EP | 1491167 | 12/2004 |
| EP | 1491168 | 12/2004 |
| EP | 1529502 | 5/2005 |
| EP | 1547549 | 6/2005 |
| EP | 1574189 | 9/2005 |
| EP | 1600183 | 11/2005 |
| EP | 1602346 | 12/2005 |
| EP | 1704833 | 9/2006 |
| EP | 1719480 | 11/2006 |
| EP | 1736123 | 12/2006 |
| EP | 1736195 | 12/2006 |
| EP | 1736202 | 12/2006 |
| EP | 1743605 | 1/2007 |
| EP | 1829504 | 9/2007 |
| EP | 1829505 | 9/2007 |
| EP | 1829506 | 9/2007 |
| EP | 1949875 | 7/2008 |
| EP | 1967168 | 9/2008 |
| EP | 1922316 | 11/2008 |
| EP | 1992315 | 11/2008 |
| EP | 1992316 | 11/2008 |
| EP | 2074970 | 7/2009 |
| EP | 2074971 | 7/2009 |
| EP | 2074972 | 7/2009 |
| EP | 2095796 | 9/2009 |
| EP | 2095797 | 9/2009 |
| EP | 2095798 | 9/2009 |
| EP | 2191796 | 6/2010 |
| FR | 1566202 | 5/1969 |
| FR | 2688693 | 9/1993 |
| FR | 2769491 | 4/1999 |
| FR | 2783153 | 3/2000 |
| FR | 2797181 | 2/2001 |
| FR | 2799118 | 4/2001 |
| FR | 2823663 | 10/2002 |
| FR | 2855744 | 12/2004 |
| FR | 2921822 | 4/2009 |
| GB | 1174814 | 12/1969 |
| GB | 2090747 | 7/1982 |
| JP | 57-171676 | 10/1982 |
| JP | 1-67309 | 4/1989 |
| JP | 2-019147 | 1/1990 |
| JP | 2-132104 | 11/1990 |
| JP | 3-105702 | 11/1991 |
| JP | 11-244395 | 9/1999 |
| JP | 2003-526410 | 9/2003 |
| JP | 2005-131380 | 5/2005 |
| JP | 2005-334658 | 12/2005 |
| SE | 8503144 | 12/1986 |
| WO | WO 86/00079 | 1/1986 |
| WO | WO 86/00912 | 2/1986 |
| WO | WO 89/11701 | 11/1989 |
| WO | WO 90/00369 | 1/1990 |
| WO | WO 92/20349 | 11/1992 |
| WO | WO 94/02517 | 2/1994 |
| WO | WO 96/33751 | 1/1996 |
| WO | WO 98/35639 | 8/1998 |
| WO | WO 98/35640 | 8/1998 |
| WO | WO 00/00108 | 1/2000 |
| WO | WO 00/01428 | 1/2000 |
| WO | WO 00/09047 | 2/2000 |
| WO | WO 00/09049 | 2/2000 |
| WO | WO 00/15158 | 3/2000 |
| WO | WO 00/66196 | 11/2000 |
| WO | WO 01/10359 | 2/2001 |
| WO | WO 01/12078 | 2/2001 |
| WO | WO 01/41671 | 6/2001 |
| WO | WO 01/47435 | 7/2001 |
| WO | WO 01/47575 | 7/2001 |
| WO | WO 01/49245 | 7/2001 |
| WO | WO 01/52777 | 7/2001 |
| WO | WO 01/68007 | 9/2001 |
| WO | WO 01/85071 | 11/2001 |
| WO | WO 02/05753 | 1/2002 |
| WO | WO 02/09792 | 2/2002 |
| WO | WO 02/19953 | 3/2002 |
| WO | WO 02/26317 | 4/2002 |
| WO | WO 02/053093 | 7/2002 |
| WO | WO 02/065948 | 8/2002 |
| WO | WO 02/096326 | 12/2002 |
| WO | WO 03/007782 | 1/2003 |
| WO | WO 03/055420 | 7/2003 |
| WO | WO 03/057092 | 7/2003 |
| WO | WO 03/059215 | 7/2003 |
| WO | WO 03/077191 | 9/2003 |
| WO | WO 03/101352 | 12/2003 |
| WO | WO 03/105732 | 12/2003 |
| WO | WO 2004/014245 | 2/2004 |
| WO | WO 2004/019671 | 3/2004 |
| WO | WO 2004/108025 | 12/2004 |
| WO | WO 2004/112563 | 12/2004 |
| WO | WO 2005/007232 | 1/2005 |
| WO | WO 2005/009305 | 2/2005 |
| WO | WO 2005/067994 | 5/2005 |
| WO | WO 2005/072195 | 8/2005 |
| WO | WO 2005/087147 | 9/2005 |
| WO | WO 2005/094447 | 10/2005 |
| WO | WO 2005/112888 | 12/2005 |
| WO | WO 2006/040647 | 4/2006 |
| WO | WO 2006/049725 | 5/2006 |
| WO | WO 2006/083885 | 8/2006 |
| WO | WO 2006/108203 | 10/2006 |
| WO | WO 2007/067206 | 6/2007 |
| WO | WO 2007/081304 | 7/2007 |
| WO | WO 2007/106727 | 9/2007 |
| WO | WO 2007/114905 | 10/2007 |
| WO | WO 2007/145638 | 12/2007 |
| WO | WO 2008/063673 | 5/2008 |
| WO | WO 2008/134755 | 11/2008 |
| WO | WO 2009/023247 | 2/2009 |
| WO | WO 2009/050709 | 4/2009 |
| WO | WO 2009/132127 | 10/2009 |
| WO | WO 2009/136126 | 11/2009 |
| WO | WO 2010/042493 | 4/2010 |

OTHER PUBLICATIONS

Brown et al; "Symmetrical Pouch Dilation After Laparoscopic Adjustable Gastric Banding: Incidence and Management"; Obesity Surgery; V. 18, pp. 1104-1108; 2008.
Ceelen et al.; "Surgical Treatment of Severe Obesity With a Low-Pressure Adjustable Gastric Band: Experimental Data and Clinical Results in 625 Patients"; Annals of Surgery; V. 237, No. 1; pp. 10-16; 2003.
Dixon et al.; "Pregnancy After Lap-Band Surgery: Management of the Band to Achieve Healthy Weight Outcomes"; Obesity Surgery; V. 11, pp. 59-65; 2001.
Neary et al.; "Peptide YY(3-36) and Glucagon-Like Peptide-$1_{(7-36)}$ Inhibit Food Intake Additively"; Endocrinology; V.146; pp. 5120-5127; 2005.
Padidela et al.; "Elevated basal and post-feed glucagon-like petide 1 (GLP-1) concentrations in the neonatel period"; European Journal of Endocrinology; v. 160; pp. 53-58; 2009.
Shi et al.; "Sexually Dimorphic Responses to Fat Loss After Caloric Restriction or Surgical Lipectomy"; Am. J. Physiol. Endocrinol. Metab.; V. 293; E316-E326; 2007.
Xanthakos et al.; "Bariatric Surgery for Extreme Adolescent Obesity: Indications, Outcomes, and Physiologic Effects on the Gut-Brain Axis"; Pathophysiology; V. 15; pp. 135-146; 2008.
"Innovative medical devices and implants"; LGSP medical futures, p. 5.

(56) References Cited

OTHER PUBLICATIONS

Acuna-Goycolea et al.; "Mechanism of Neuropeptide Y, Peptide YY, and Pancreatic Polypeptide Inhibition of Identified Green Fluorescent Protein-Expressing GABA Neurons in the Hypothalamic Neuroendocrine Acruate Nucleus"; The Journal of Neuroscience; V. 25(32); pp. 7406-7419; Aug. 10, 2005.
Adrian et al.; "Mechanism of Pancreatic Polypeptide Release in Man." The Lancet; pp. 161-163; Jan. 22, 1977.
Anson; "Shape Memory Alloys—Medical Applications," Source: Materials World, vol. 7, No. 12, pp. 745-747, Dec. 1999.
Asakawa et al; "Antagonism of Ghrelin Receptor Reduces Food Intake and Body Weight Gain in Mice"; Gut.; V.52; pp. 947-952; 2003.
Baggio et al. "Biology of Incretins: GLP-1 and GIP"; Gastroenrology; V. 132; pp. 2131-2157; 2007.
Ballantyne; "Peptide YY(1-36) and Peptide YY(3-36): Part I. Distribution, Release, and Actions"; Obesity Surgery; V.16; pp. 651-658; 2006.
Ballantyne; "Peptide YY(1-36) and Peptide YY(3-36): Part II. Changes after Gastrointestinal Surgery and Bariatric Surgery"; Obesity Surgery; V.16; pp. 795-803; 2006.
Berne et al; "Physiology"; V. 5; pp. 55-57, 210, 428, 540, 554, 579, 584, 591; 2004.
BioEnterics Lap-Band Adjustable Gastric Banding System, Inamed Health, pub., pp. 1-115; Aug. 28, 2003.
Boulant et al.; "Cholecystokinin in Transient Lower Oesophageal Sphincter Relaxation Due to Gastric Distension in Humans"; Gut.; V. 40; pp. 575-581; 1997.
Bradjewin et al.; "Dose Ranging Study of the Effects of Cholecystokinin in Healthy Volunteers"; J. Psychiatr. Neurosci.; V. 16 (2); pp. 91-95; 1991.
Burdyga et al.; "Cholecystokinin Regulates Expression of Y2 Receptors in Vagal Afferent Neurons Serving the Stomach"; The Journal of Neuroscience; V. 28; No. 45; pp. 11583-11592; Nov. 5, 2008.
Chaptini et al.; "Neuroendocrine Regulation of Food Intake"; Current Opinion in Gastroenterology; V. 24; pp. 223-229; 2008.
Chaudhri; "Can Gut Hormones Control Appetite and Prevent Obesity?" Diabetes Care; V. 31; Supp 2; pp. S284-S289; Feb. 2008.
Cohen et al.; "Oxyntomodulin Suppresses Appetite and Reduces Food Intake in Humans"; J. Clin. Endocrinol. Metab.; V. 88; No. 10; pp. 4696-4701; 2003.
Corno et al.; "A new implantable device for telemetric control of pulmonary blood flow"; New ideas; received Apr. 24, 2004; received in revised form Jul. 12, 2002; 10 pages.
Corno et al.; "FlowWatchTM in clipped and inclipped position"; Interact Cardio Vase Thorac Surg 2002; 1:46-49; Copyright @ 2002 The European Association for Cardio-thoracic Surgery; 1 page.
Cummings et al.; "Plasma Ghrelin Levels After Diet-Induced Weight Loss or Gastric Bypass Surgery"; N. Engl J. Med; V. 346, No. 21; pp. 1623-1630; May 23, 2002.
Cummings; "Gastrointestinal Regulation of Foot Intake"; The Food Journal of Clinical Investigation; V. 117, N. 1; pp. 13-23; Jan. 2007.
Dakin et al.; "Oxyntomodulin Inhibits Food Intake in the Rat"; Endocrinology; V. 142; No. 10; pp. 4244-4250; 2001.
Dakin et al.; "Peripheral Oxyntomodulin Reduces Food Intake and Body Weight gain in Rats"; Endocrinology; V. 145; No. 6; pp. 2687-2695; Jun. 2004.
Davison; "Activation of Vagal-Gastric Mechanoreceptors by Cholecystokinin"; Proc. West. Pharmocol. Soc.; V. 29; pp. 363-366; 1986.
De Waele et al.; "Endoscopic Volume Adjustment of Intragastric Balloons for Intolerance"; Obesity Surgery; V. 11; pp. 223-224; 2001.
De Waele et al.; "Intragastric Balloons for Preoperative Weight Reduction"; Obesity Surgery; V. 58; pp. 58-60; 2001.
Desai et al.; "Molecular Weight of Heparin Using 13C Nuclear Magnetic Resonance Spectroscopy" Journal of Pharmaceutical Science, V. 84, I 2; 1995, Abstract only.

Doldi et al.; "Intragastric Balloon: Another Option for Treatment of Obesity and Morbid Obesity"; Hepato-Gastroenterology; V. 51, N. 55; pp. 294-307; Jan.-Feb. 2004.
Doldi et al.; "Treatment of Morbid Obesity with Intragastric Balloon in Association with Diet"; Obesity Surgery; V. 10, pp. 583-587; 2000.
Doldi et al; "Intragastric Balloon in Obese Patients"; Obesity Surgery; V. 10, 578-581; 2000.
Ekblad et al.; "Distribution of Pancreatic Peptide and Peptide-YY"; Peptides; V. 23; pp. 251-261; 2002.
El Khoury et al.; "Variation in Postprandial Ghrelin Status Following Ingestion of High-Carbohydrate, High Fat, and High Protein Meals in Males"; Ann Nutr Metab; V. 50; pp. 260-269; 2006.
Galloro et al; "Preliminary Endoscopic Technical Report of an New Silicone Intragastric Balloon in the Treatment of Morbid Obesity"; Obesity Surgery; V. 9, pp. 68-71; 1999.
GinShiCel MH Hydroxy Propyl Methyl Cellulose, Web Page http://www.ginshicel.cn/MHPC.html, Nov. 12, 2008.
Girard; "The incretins: From the concept to their use in the treatment of type 2 diabetes. Part A: Incretins: Concept and physiological functions"; Diabetes and Metabolism; V. 34; pp. 550-559; 2008.
Greenough et al.; "Untangling the Effects of Hunger, Anxiety, and Nausea on Energy Intake During Intravenous Cholecystokinin Octapeptide (CCK-8) Infusion"; Physiology & Behavior; V. 65, No. 2; pp. 303-310; 1998.
Grise et al.; "Peptide YY Inhibits Growth of Human Breast Cancer in Vitro and in Vivo"; Journal of Surgical Research; V. 82; pp. 151-155; 1999.
Grundy; "Signaling the State of the Digestive Tract"; Autonomic Neuroscience: Basic and Clinical; V. 125; pp. 76-80; 2006.
Grundy; "Vagal Control of Gastrointestinal Function"; Bailliere's Clinical Gastroenterology; V. 2; No. 1; pp. 23-43; 1988.
Hallden et al. "Evidence for a Role of the Gut Hormone PYY in the Regulation of Intestinal Fatty Acid Binding Protein Transcripts in Differentiated Subpopulations of Intestinal Epithelial Cell Hybrids"; Journal of Biological Chemistry; V. 272 (19); pp. 125916-126000; 1997.
Hameed et al.; "Gut hormones and appetite control." Oral Diseases; V. 15; pp. 18-26; 2009.
Hassan et al.; "Effects of Adjuvants to Local Anesthetics on Their Duration III Experimental Studies of Hyaluronic Acid" Abstract Pub Med [Acta Anesthesiol Scand.; 29 (4): 384-8], 1 page; May 1985.
Hodson et al.; "Management of Obesity with the New Intragastric Balloon"; Obesity Surgery; V. 11, pp. 327-329, 2001.
Holzer; "Gastrointestinal Afferents as Targets of Novel Drugs for the Treatment of Functional Bowel Disorders and Visceral Pain"; European Journal of Pharmacology; V. 429; pp. 177-193; 2001.
Houpt; "Gastrointestinal Factors in Hunger and Satiety." Neuroscience and Behavioral Reviews; V. 6; pp. 145-164; 1982.
Jones; "Molecular, pharmacological, and clinical aspects of liraglutide, a oncedaily human GLP-1 analogue"; Molecular and Cellular Endocrinology; V. 297; pp. 137-140; 2009.
Kerem et al.; "Exogenous Ghrelin Enhances Endocrine and Exocrine Regeneration in Pancreatectomized Rats"; J Gastrointest Surg.; V.13; pp. 775-783, 2009.
Kesty et al.; "Hormone-based therapies in the regulation of fuel metabolism and body weight"; Expert Opin. Biol. Ther.; V. 8; No. 11; pp. 1733-1747; 2008.
Kissileff et al.; "Peptides that Regulate Food Intake: Cholecystokinin and Stomach Distension Combine to Reduce Food Intake in Humans"; Am. J. Physiol. Regul. Integr. Comp. Physiol; V. 285; pp. 992-998; 2003.
Kojima et al.; "A role for pancreatic polypeptide in feeding and body weight regulation." Peptides; V. 28; pp. 459-463; 2007.
Kulicke et al. "Visco-Elastic Propeerties of Sodium Hyaluronate Solutions," American Institute of Physics; pp. 585-587; 2008.
Lap-Band AP System Adjustable Gastric Banding System With OmniformTM Design: Directions for Use (DFU); Allergan, 16 pages; 2009.
Le Roux et al.; "Gut Hormone Profiles Following Bariatric Surgery Favor an Anorectic State, Facilitate Weight Loss, and Improve Metabolic Parameters"; Ann. Surg; V. 243; No. 1; pp. 108-114; Jan. 2006.

(56) References Cited

OTHER PUBLICATIONS

Liu et al.; "Adjuvant Hormonal Treatment With Peptide YY or Its Analog Decreases Human Pancreatic Carcinoma Growth"; The American Journal of Surgery; V. 171; pp. 192-196; Jan. 1996.

Mathus-Vliegen et al. "Intragastric Balloons for Morbid Obesity: Results, Patient Tolerance and Balloon Life Span"; Br. J. Surg.; V. 77, No. 7, pp. 76-79; Jan. 1990.

Mathus-Vliegen et al. "Treating Morbid and Supermorbid Obesity" International Journal of Gastroenterology; V. 5, No. 1, pp. 9-12; 2000.

Medeiros et al.; "Processing and metabolism of Peptide-YY: Pivotal roles of Dipeptidase-IV, Aminopeptidase-P, and Endopeptidase-24.11"; Endocrinology; V. 134, No. 5; pp. 2088-2094; 1994.

Naslund et al. "Pranidal subcutaneous injections of glucagon-like peptide-1 cause weight loss in obese human subjects"; British Journal of Nutrition; V. 91; pp. 439-446; 2004.

Potier et al.; "Protein, amino acids, and the control of food intake"; Current Opinion in Clinical Nutrition and Metabolic Care; V. 12; pp. 54-58; 2009.

Qjan et al.; "Pulmonary delivery of a GLP-1 receptor agonist, BMS-686117"; International Journal of Pharmaceutics; V. 366; pp. 218-220; 2008.

Rang et al.; "Pharmacology"; V. 5; pp. 203, 397, 402, 524; 2004.

Raybould et al.; "Integration of Postprandial Gastrointestinal Tract: Role of CCK and Sensory Pathways"; Annals of New York Academy of Science; pp. 143-156; 1994.

Renshaw et al. "Peptide YY: A Potential Therapy for Obesity"; Current Drug Targets; V. 6; pp. 171-179; 2005.

Sannino et al.; "Crosslinking of Cellulose Derivatives and Hyaluronic Acid with Water-Soluble Carbodiimide" Polymer 46; pp. 11206-11212; 2005.

Shechter et al.; "Reversible PEGylation of peptide YY3-36 prolongs its inhibition of food intake in mice"; FEBS Letters; V. 579; pp. 2439-2444; 2005.

Silver et al.; "Physical Properties of Hyaluronic Acid and Hydroxypropylmethylcellulose in Solution: Evaluation of Coating Abillity" Journal of Applied Biomaterials, V. 5; pp. 89-98, 1994.

Small et al.; "Gut hormones and the control of appetite"; TRENDS in Endocrinology and Metabolism; V. 15. No. 6; pp. 259-263; Aug. 2004.

Stanley et al.; "Gastrointestinal Satiety Signals III. Glucagon-like Peptide 1, oxyntomodulin, peptide YY, and pancreatic polypeptide"; Am. J. Physiol Gastrointest Liver Physiol; V. 286; pp. 693-697; 2004.

Tezel; "The Science of Hyaluronic Acid Dermal Fillers," Journal of Cosmetic and Laser Therapy (2008) 10: pp. 35-42.

Tolhurst et al.; "Nutritional regulation of glucagon-like peptide1 secretion"; J. Physiol.; V. 587, No. 1; pp. 27-32; 2009.

Totte et al.; "Weight Reduction by Means of Intragastric Device: Experience with the Bioenterics Intragastric Balloon"; Obesity Surgery; V. 11, pp. 519-523; 2001.

Tough et al.; "$Y_4$ Receptors Mediate the Inhibitory Responses of Pancreatic Polypeptide in Human and Mouse Colon Mucosa"; The Journal of Pharmacology and Experimental Therapeutics; V. 319, No. 1; pp. 20-30; 2006.

Tseng et al; "Peptide YY and cancer: Current findings and potential clinical applications"; Peptides; V. 23; pp. 389-395; 2002.

Valassi et al.; "Neuroendocrine control of food intake"; Nut. Metab. & Cariovasc. Disease; V. 18; pp. 158-168; 2008.

Van Der Lely et al.; "Biological, Physiological, Pathophysiological Aspects of Ghrelin"; Endocrine Reviews; V. 25, No. 3; pp. 426-457; 2004.

Verdich et al. "A Meta-Analysis of the Effect of Glucagon-Like-Peptide-1 (7-36) Amide on ad Libitum Energy Intake in Humans"; J. Clin. Endocrinal. Metab. V. 86; pp. 4382-4389; Sep. 2001.

Wahlen et al.; "The BioEnterics Intragastric Balloon (BIB): How to Use It"; Obesity Surgery; V. 11; pp. 524-527; 2001.

Wang et al.; "Plasma Ghrelin Modulation in Gastric Band Operation and Sleeve Gastrectomy"; Obes. Surg.; pp. 357-362; 2008.

Weiner et al.; "Preparation of Extremely Obese Patients for Laparoscopic Gastric Banding by Gastric Balloon Therapy"; Obesity Surgery; V. 9, pp. 261-264, 1999.

Wynne et al.; "Subcutaneous Oxyntomodulin Reduces Body Weight in Overweight and Obese Subjects: A Double-Blind Randomized, Controlled Trial"; Diabetes; V. 54; pp. 2390-2395; 2005.

Yuzuriha et al.; "Gastrointestinal Hormones (anorexigenic peptide YY and orexigenic ghrelin) influence neural tube development"; FASEB J.; V. 21; pp. 2108-2112; 2007.

\* cited by examiner

PRESSURE SENSING GASTRIC BANDING SYSTEM

FIELD

The present invention generally relates to medical systems and apparatus and uses thereof for treating obesity and/or obesity-related diseases, and more specifically, relates to pressure sensing for gastric banding systems.

BACKGROUND

Adjustable gastric banding apparatus have provided an effective and substantially less invasive alternative to gastric bypass surgery and other conventional surgical weight loss procedures. Despite the positive outcomes of invasive weight loss procedures, such as gastric bypass surgery, it has been recognized that sustained weight loss can be achieved through a laparoscopically-placed gastric band, for example, the LAP-BAND® (Allergan, Inc., Irvine, Calif.) gastric band or the LAP-BAND AP® (Allergan, Inc., Irvine, Calif.) gastric band. Generally, gastric bands are placed about the cardia, or upper portion, of a patient's stomach forming a stoma that restricts the food's passage into a lower portion of the stomach. When the stoma is of an appropriate size that is restricted by a gastric band, food held in the upper portion of the stomach provides a feeling of satiety or fullness that discourages overeating. Unlike gastric bypass procedures, gastric band apparatus are reversible and require no permanent modification to the gastrointestinal tract.

Over time, a stoma created by a gastric band may need adjustment in order to maintain an appropriate size, which is neither too restrictive nor too passive. Accordingly, prior art gastric band systems provide a subcutaneous fluid access port connected to an expandable or inflatable portion of the gastric band. By adding fluid to or removing fluid from the inflatable portion, for example, by means of a hypodermic needle inserted into the access port, the effective size of the gastric band can be adjusted to provide a tighter or looser constriction. The level of constriction is related to the amount of fluid in the gastric band system. The level of constriction is also related to the pressure within the gastric band system.

An implantable pressure sensor for monitoring blood pressure is disclosed in U.S. Pat. No. 5,120,313 to Elftman. However, the system of Elftman is percutaneous and extends partially outward from the skin, and is thus unsuitable for complete implantation.

A previous attempt to provide a medical pressure sensor may be found in U.S. Pat. No. 5,554,113 to Novak et al. While the Novak sensor is sterilizable, it is not fully implantable and requires a percutaneous conduit.

Other attempts to provide a medical pressure sensor may be found in U.S. Pat. No. 6,024,704 to Meador et al. and in U.S. Pat. No. 5,535,752 to Halperin et al. However, although the sensors of Meador and Halperin are implantable, they are energized by an implanted battery, and both are specifically intended for use within the heart and in connection with an implanted pulse generator.

Yet another attempt to provide a medical pressure sensor may be found in U.S. Pat. No. 6,221,024 to Miesel. The sensor of Miesel utilizes an incompressible oil as a pressure transfer medium, but does not address minimizing damaged caused by thermal expansion.

Still another attempt to provide a medical pressure sensor may be found in U.S. Pat. No. 7,021,147 to Subramanian et al. The sensor of Subramanian addresses thermal expansion but limits the scope to utilizing fillers with low or negative coefficients of thermal expansion.

A prior attempt to provide pressure monitoring for a gastric banding system may be found in U.S. Patent Application Publication No. 2006/0189888 by Hassler et al. However, the pressure sensor of Hassler is specifically part of the access port, and thus does not permit the pressure sensor to be used with preexisting access ports.

Another prior attempt to provide pressure monitoring for a gastric banding system may be found in U.S. Patent Application Publication No. 2008/0221598 by Dlugos et al. However, the pressure sensors of Dlugos do not confer strain relief or puncture resistance features.

It remains desirable to monitor pressure within a gastric band system. Thus, tubing-based pressure sensors for gastric banding systems are described herein.

SUMMARY

Generally described herein are pressure sensors for gastric band systems, and methods of use thereof. The apparatus, systems and methods described herein aid in facilitating obesity control and/or treating obesity-related diseases, and may be non-invasive once implanted.

In one embodiment, an implantable device is configured for monitoring static and fluctuating pressure levels of a fluid moving to and from an inflatable portion of a gastric band. The implantable device comprises a housing defining a cavity and having an open top portion, and a flexible membrane covering the open top portion of the housing and having an inner surface facing the cavity and an outer surface capable of contacting the fluid. The implantable device further comprises a pressure transfer fluid located within the cavity, and a sensing element, positioned within the cavity of the housing and positioned adjacent to the flexible membrane. The sensing element measures a pressure on the flexible membrane. The pressure is caused by the fluid contacting the outer surface of the flexible membrane. The sensing element converts the pressure to a pressure signal.

The implantable device further comprises a microcontroller positioned within the cavity of the housing and coupled to the sensing element. The microcontroller is configured to transmit the pressure signal received from the sensing element to a location external to the implantable device.

In another embodiment, an implantable device is configured to monitor a pressure of fluid within an inflatable portion of a gastric band. The implantable device comprises a tube defining a lumen and having a first end and a second end. The second end is connected to the inflatable portion of the gastric band for allowing the fluid to flow through the lumen. The implantable device further comprises a pressure sensor positioned within at least one of the lumen or the tube. The pressure sensor is configured to sense the pressure of the fluid within the inflatable portion of the gastric band, and the pressure sensor is configured to transmit a pressure signal based on the pressure to a remote control device. Further, the pressure sensor comprises a rigid housing conferring strain relief upon at least a portion of the tube, and the pressure sensor shields at least a portion of the tube from puncture by a needle.

In another embodiment, a system is configured to facilitate obesity control. The system comprises an implantable gastric banding device including an inflatable member for containing fluid and restricting a patient's cardia, and an implantable access port coupled to the implantable gastric banding device via tubing. The implantable access port is configured to control pressure within the inflatable member.

The system further comprises an external remote control device capable of communicating with and powering a pressure sensor and the pressure sensor disposed at least partially within the tubing. The pressure sensor comprises a housing defining a cavity and having an open top portion, and a flexible membrane covering the open top portion of the housing and having an inner surface facing the cavity and an outer surface capable of contacting a fluid within the tubing.

The pressure sensor further comprises a pressure transfer fluid located within the cavity, and a sensing element, positioned within the cavity of the housing and positioned adjacent to the flexible membrane. The sensing element is configured to measure a pressure on the flexible membrane. The pressure is caused by the fluid contacting the outer surface of the flexible membrane. The pressure sensor is configured to convert the pressure to a pressure signal, and to transmit the pressure signal to a remote device.

In another embodiment, a system is configured to facilitate obesity control. The system comprises an implantable gastric banding device including an inflatable member for containing fluid and restricting a patient's cardia, an implantable fluid reservoir, and an implantable pump unit for controlling pressure within the inflatable member. The implantable pump unit is in communication with the fluid reservoir and the gastric banding device via tubing.

The system further comprises an implantable access port coupled to the implantable pump unit, an external remote control device capable of communicating with and powering the implantable pump unit and a pressure sensor, and the pressure sensor disposed at least partially within the tubing.

The pressure sensor comprises a housing defining a cavity and having an open top portion, and a flexible membrane covering the open top portion of the housing and having an inner surface facing the cavity and an outer surface capable of contacting a fluid within the tubing.

The pressure sensor further comprises a pressure transfer fluid located within the cavity, and a sensing element, positioned within the cavity of the housing and positioned adjacent to the flexible membrane. The sensing element is configured to measure a pressure on the flexible membrane. The pressure is caused by the fluid contacting the outer surface of the flexible membrane. The pressure sensor is configured to convert the pressure to a pressure signal. The pressure sensor further comprises a microcontroller positioned within the cavity of the housing and coupled to the sensing element. The microcontroller is configured to process the pressure signal received from the sensing element and transmit the processed pressure signal to a remote device.

In another embodiment, a method of retrofitting a tubing-based pressure sensor to a previously implanted gastric banding system is provided. The method comprises removing a portion of existing tubing from the gastric banding system, and inserting a portion of new tubing into the gastric banding system. The portion of the new tubing contains at least one pressure sensor disposed at least partially therein.

The pressure sensor comprises a housing defining a cavity and having an open top portion, and a flexible membrane covering the open top portion of the housing and having an inner surface facing the cavity and an outer surface capable of contacting a fluid within the tubing.

The pressure sensor further comprises a pressure transfer fluid located within the cavity, and a sensing element, positioned within the cavity of the housing and positioned adjacent to the flexible membrane. The sensing element is configured to measure a pressure on the flexible membrane. The pressure is caused by the fluid contacting the outer surface of the flexible membrane. The pressure sensor is configured to convert the pressure to a pressure signal. The pressure sensor further comprises a microcontroller positioned within the cavity of the housing and coupled to the sensing element. The microcontroller is configured to process the pressure signal received from the sensing element and transmit the processed pressure signal to a location external to the pressure sensor.

The method further comprises coupling the portion of the new tubing to at least one of: a previously implanted access port, a previously implanted pump, or a portion of the existing tubing.

DETAILED DESCRIPTION

The present invention generally provides pressure sensing for gastric banding systems, for example, for treatment of obesity and obesity related conditions.

Figure 1A:
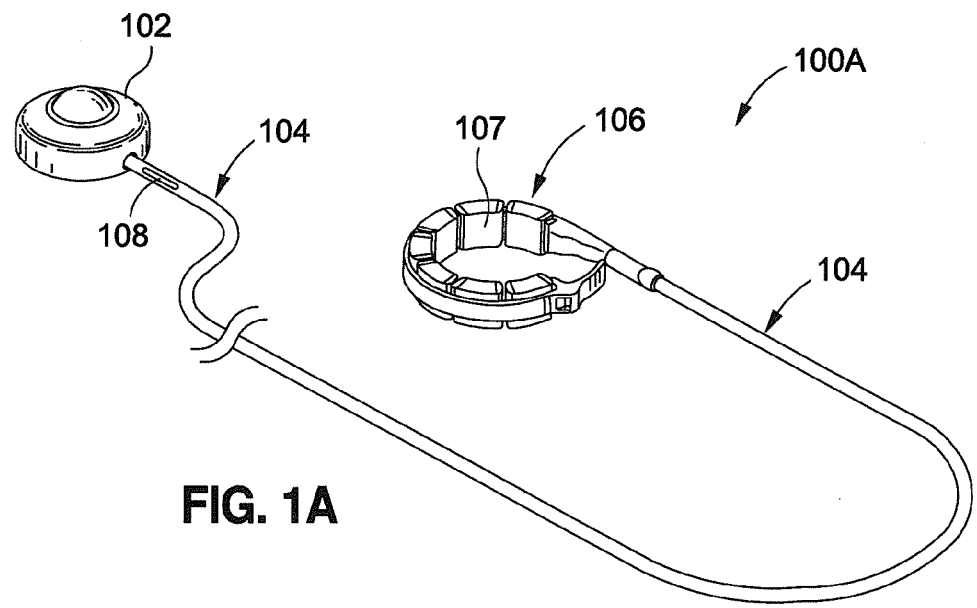
FIG. 1A illustrates an overall schematic view of an example configuration of components according to an embodiment of the present invention.

Turning now to FIG. 1A, a gastric banding system 100A in accordance with one embodiment of the present invention generally includes an access port 102, a tubing 104, a gastric band 106 having at least one inflatable member 107, a pressure sensor 108, and a remote controller unit 110 (not shown). Each of the components of the system 100A, other than the remote controller unit 110, is implantable in a patient using conventional surgical techniques. The access port 102 may be used, for example, with a hypodermic needle, to fill and drain the gastric band 106, for example responsive to pressure measured by the pressure sensor 108 and communicated to the remote controller unit 110.

Figure 1B:
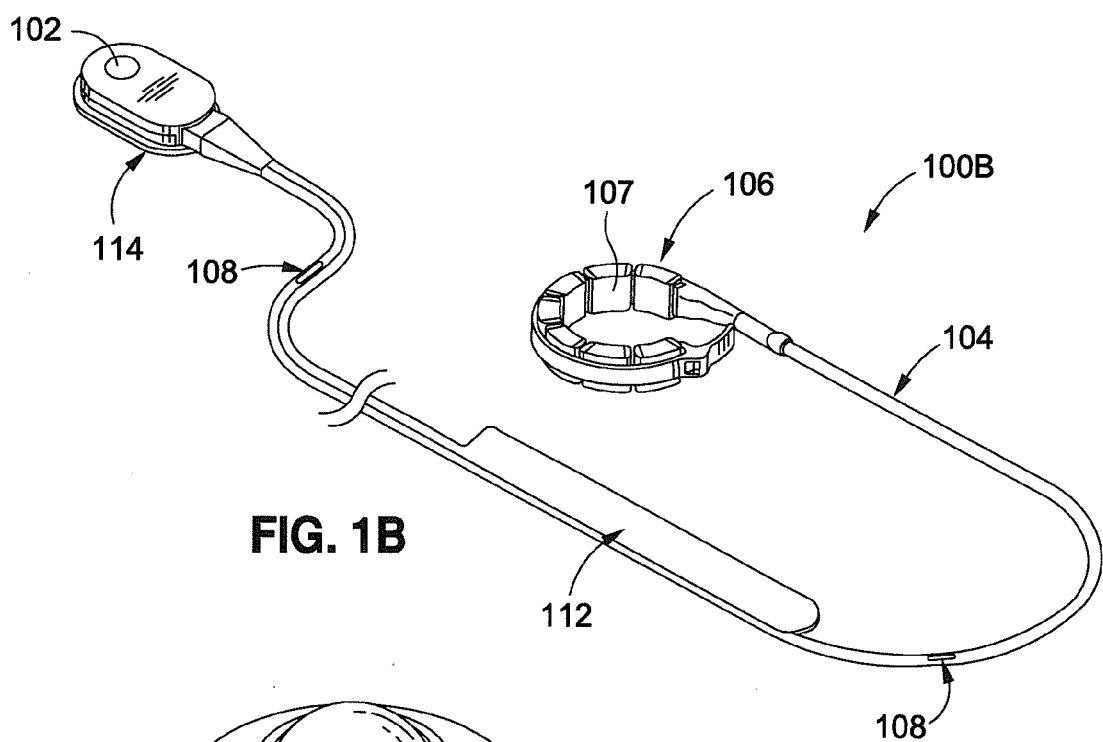
FIG. 1B illustrates an overall schematic view of an example configuration of components according to an embodiment of the present invention.

Turning now to FIG. 1B, a gastric banding system 100B in accordance with another embodiment of the present invention generally includes an access port 102, a tubing 104, a gastric band 106 having at least one inflatable member 107, a pressure sensor 108, a remote controller unit 110 (not shown), a reservoir 112, and a high precision pump unit 114. Each of the components of the system 100B, other than the remote controller unit 110, is implantable in a patient using conventional surgical techniques. The high precision pump unit 114 can be used to complement or replace the access port 102 for adjusting inflation of the gastric band 106, for example, responsive to pressure measured by the pressure sensor 108. The high precision pump 114 may also include a microcontroller or a microprocessor to receive a telemetric signal from the remote controller unit 110. The microcontroller or the microprocessor may be used to the control the high precision pump 114.

With reference to FIGS. 1A and 1B, in various example embodiments, one or more pressure sensors 108 are coupled to the tubing 104. When compared to conventional gastric banding systems having no pressure sensing components, or having pressure sensing components integrated into access ports, pumps, and/or the like, the presently described systems and apparatus offer several benefits. By locating the pressure sensor 108 within the wall of the tubing 104 and/or within the tubing 104 lumen, the tubing 104 incorporating the pressure sensor 108 may be easily retrofitted to preexisting access ports. Additionally, by locating the pressure sensor 108 within the wall of the tubing 104 and/or within the tubing 104 lumen, interference between the pressure sensor 108 and electrical and/or mechanical components of an access port, a pump, a valve, or other components of a gastric banding system may be reduced and/or eliminated, for example due to increased spacing between the pressure sensor 108 and other components. Further, locating the pressure sensor 108 within the wall of the tubing 104 allows the pressure sensor 108 to confer additional puncture resistance to at least the corresponding portion of the tubing 104. Moreover, utilization of a substantially rigid pressure sensor 108 and/or associated hard connectors and/or other components allows the pressure sensor 108 to act as partial strain relief for the tubing 104.

Further, by locating the pressure sensor 108 away from the access port, the pump, the valves, and/or other components of a gastric banding system, certain electrical portions of the pressure sensor 108, such as antenna, are not affected by metal parts which may be in such other components of a gastric banding system. In this manner, the pressure sensor 108 can achieve improved powering and/or communication ranges due to the reduced interference.

Referring again to FIG. 1B, in an example embodiment, the high precision pump unit 114 is connected to the reservoir 112 and the gastric band 106 via the tubing 104, and can move precisely metered volumes of fluid in or out of the gastric band 106. Moving the fluid into the gastric band 106 causes inflation of at least one bladder, or inflatable member 107 of the gastric band 106 and constricts around the cardia, or upper portion of the stomach, forming a stoma that restricts the passage of food into a lower portion of the stomach. This stoma can provide a patient with a sensation of satiety or fullness that discourages overeating. In contrast, moving fluid out of the at least one inflatable member 107 of the gastric band 106 contracts the pressure around the cardia and allows a stoma to be at least partially released and regains the patient's hunger sensation.

The high precision pump unit 114 is implanted within a patient, and therefore, is non-biodegradable. The encasement of the high precision pump unit 114 may be non-hermetically or hermetically sealed from the in situ environment and at least partially formed of any rugged plastic material, including polypropylene, cyclicolefin co-polymer, nylon, and other compatible polymers and the like, or at least partially formed of a non-radioopaque metal. The encasement has a smooth exterior shape, with no jagged edges, to minimize foreign body response and tissue irritation. The unit itself is also sterilizable, preferably dry heat sterilizable before implantation.

In one example embodiment, the encasement or housing of the high precision pump unit 114 has an internal volume of between about 0.75 in$^3$ to about 1.6 in$^3$. The high precision pump unit 114 can be arranged in any fashion appropriate for delivering and removing precise amounts of fluid from the gastric band 106 and the reservoir 112.

The high precision pump unit 114 can be actively or passively driven. If the high precision pump unit 114 is actively driven, a local power source such as a battery (not shown) is provided to drive the high precision pump unit 114. If the high precision pump unit 114 is passively driven, it may be inductively powered by a device external to the high precision pump unit 114. In an exemplary configuration, the high precision pump unit 114 is passively driven through inductive power, for example, power delivered by the remote controller unit 110. In one example embodiment, the high precision pump unit 114 is an inductively powered, electrically driven, positive displacement piezoelectric pump. The high precision pump unit 114 provides one means to move fluid into and/or out of the gastric band 106 and/or the reservoir 112.

In an example embodiment, the high precision pump unit 114 can move fluid from the reservoir 112 to the gastric band 106 at rates higher than about 0.5 cc/min, for example higher than about 1 cc/min for band pressures less than about 10 psi (about 138 kPa) relative to the reservoir pressure. Alternatively, fluid can be drained from the gastric band 106 to the reservoir 112 at rates higher than about 0.5 cc/min, for example, higher than about 1 cc/min for band pressures above about 0.2 psi (about 1.38 kPa).

Additional details regarding adjustable gastric banding systems and exemplary components thereof may be found in Birk, U.S. Patent Application Publication No. 2009/0270904, and Birk, U.S. Patent Application Publication No. 2007/0156013, each of which are commonly assigned herewith and incorporated in their entirety herein by this specific reference.

In an example embodiment, the reservoir 112 is a soft, collapsible balloon made of a biocompatible polymer material, for example, silicone, which holds a reserve of a biocompatible fluid, for example, saline, to allow for adjustments in the size of the gastric band 106. The reservoir 112 is preferably fully collapsible and can contain the extra fluid required to increase the volume of the gastric band 106 to therapeutic levels. Further, the reservoir 112 also may have excess capacity so the gastric band 106 may be fully drained into it without the reservoir 112 being filled beyond its maximum capacity.

The fluids used within the systems include any fluid that is biocompatible. Consequently, the fluid has no adverse effect on the patient in the unlikely event that a leak emanates from the system. The fluid can simply be water or any biocompatible polymer oil such as castor oil. In an example embodiment, the fluid is saline.

The tubing 104 is any biocompatible flexible tubing that does not degrade in vivo. The tubing 104 is configured to withstand hydraulic forces up to about 30 psi (about 206 kPa) without leakage. This hydraulic pressure tolerance is true of the entire fluid path of the systems described herein. Although the systems described herein do not generally leak, if they do, in general fluid is not lost at a rate greater than about 0.2 cc/yr, or about 0.1 cc/yr.

Other biocompatible and biostable polymers which are useful for forming the reservoir 112 and/or the tubing 104 include polyolefins, polyisobutylene and ethylene-alphaolefin copolymers; acrylic polymers and copolymers, ethylene-co-vinylacetate, polybutylmethacrylate, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

Figure 2:
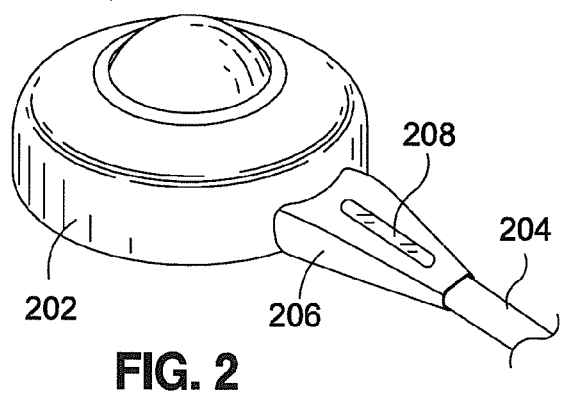
FIG. 2 illustrates a pressure sensor disposed in a strain relief portion located between an access port and tubing in an example configuration of components according to an embodiment of the present invention.

Turning now to FIG. 2, in an example embodiment, an access port 202 is coupled to a tubing 204 via a strain relief portion 206. A pressure sensor 208 is disposed within the strain relief portion 206. The strain relief portion 206 may comprise a thickened portion of the tubing 204; alternatively, the strain relief portion 206 may comprise a material different from the tubing 204. In these embodiments, the pressure sensor 208 may be disposed within the strain relief portion 206 in a location configured to allow the pressure sensor 208 to detect changes in the pressure in the fluid passing through the strain relief portion 206 and/or the tube 204. Additionally, the strain relief portion 206 and/or the pressure sensor 208 help protect the tubing 204 from errant needle sticks, for example, needle sticks intended to contact the nearby access port 202. For example, the pressure sensor 208 may comprise material resistant to puncture by a sharp object.

Moreover, in accordance with principles of the present invention, a pressure sensor may be integrated into and/or coupled to the tubing 104 in any suitable manner. For example, various configurations of a pressure sensor 308 as integrated into and/or contained within a tubing 304 are illustrated in FIGS. 3A through 3D. In one example embodiment illustrated in FIG. 3A, at least a portion of the tubing 304 has a generally rectangular cross-section and defines an inner lumen 310. The pressure sensor 308 is disposed within the tubing 304 adjacent to the lumen 310. In this configuration, the pressure sensor 308 and the lumen 310 may be aligned "side by side" with respect to the skin of a patient.

Figure 3A:
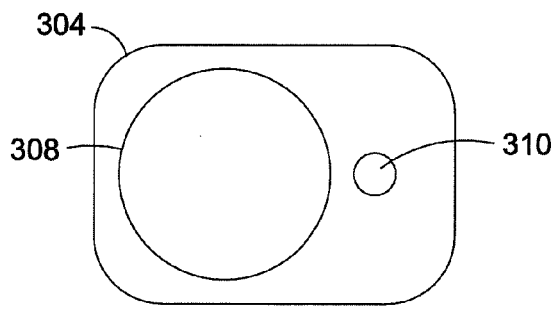
FIGS. 3A through 3D illustrate cross-sections of an example tubing incorporating a pressure sensor according to an embodiment of the present invention.
Figure 3B:
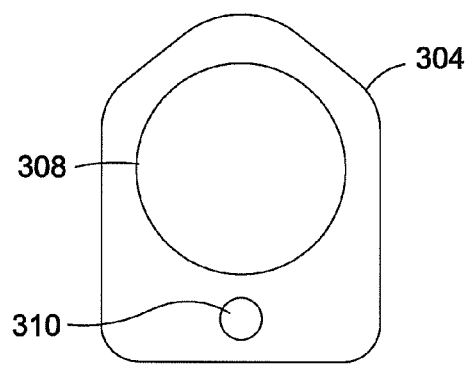

In another example embodiment illustrated in FIG. 3B, at least a portion of the tubing 304 has a somewhat "bullet"-shaped cross section and defines an inner lumen 310. The pressure sensor 308 is disposed within the tubing 304 adjacent to the lumen 310. In this configuration, the pressure sensor 308 and the lumen 310 may be aligned "top and bottom" with respect to the skin of a patient. In this manner, the pressure sensor 308 and/or the tubing 304 may at least partially protect the lumen 310 from damage or puncture, for example, from errant needle sticks. Moreover, any suitable cross-sections of the tubing 304 and/or the pressure sensor 308 may be aligned "top to bottom" in order to locate the pressure sensor 308 at least partially between a portion of the lumen 310 and an incoming needle or other device which may potentially damage the tubing 304.

Figure 3C:
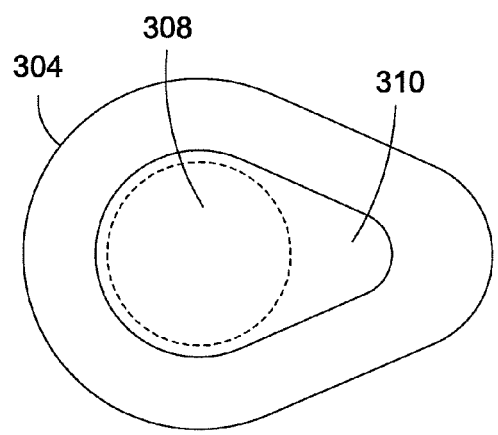

In another example embodiment illustrated in FIG. 3C, at least a portion of the tubing 304 has a somewhat "egg"-shaped cross section and defines a similarly shaped inner lumen 310. In this configuration, the tubing 304 may also be considered to have a cross-section resembling a conical frustum configured with partially rounded edges. The pressure sensor 308 is disposed within the lumen 310. In this manner, the pressure sensor 308 may be in direct contact with the fluid contained in the lumen 310 while still allowing flow of the fluid through the lumen 310, for example, when the pressure sensor 308 is configured with a substantially circular cross-section or other cross-section different from the cross-section of the lumen 310.

Figure 3D:
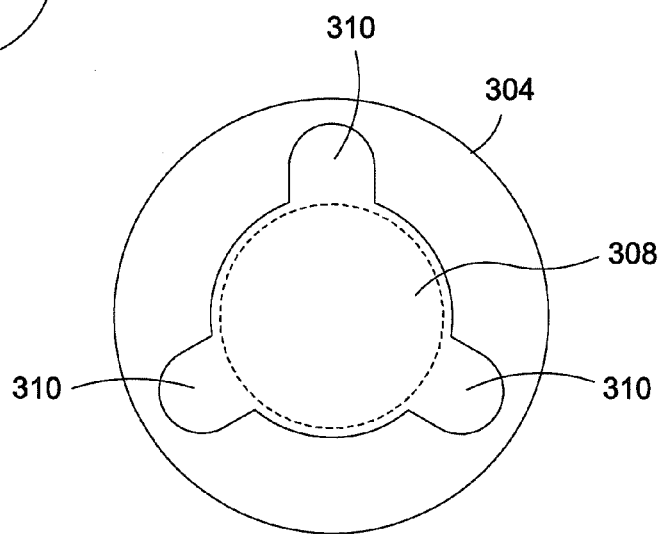

In another example embodiment illustrated in FIG. 3D, at least a portion of the tubing 304 has a circular cross-section. Within the tubing 304, an inner lumen 310 having a cross-section with a main lumen area and a plurality of extensions therefrom is defined. The pressure sensor 308 is disposed within the main lumen area of the lumen 310. In this manner, the pressure sensor 308 may be in direct contact with the fluid contained in the lumen 310 while not obstructing flow of the fluid through the lumen 310 even when the tubing 304 is bent or kinked. For example, when the tubing 304 is bent in a particular direction, one or more of the plurality of extensions from the main lumen area of the lumen 310 may be at least partially blocked, while fluid flow through another of the plurality of extensions may remain substantially unrestricted.

Moreover, it will be appreciated by one of ordinary skill in the art that many additional shapes, geometries, configurations, cross-sections, and/or combinations of the tubing 304, the inner lumen 310, and the pressure sensor 308 and/or additional components are possible, and all such are considered to be within the scope of the present invention.

Figure 4A:
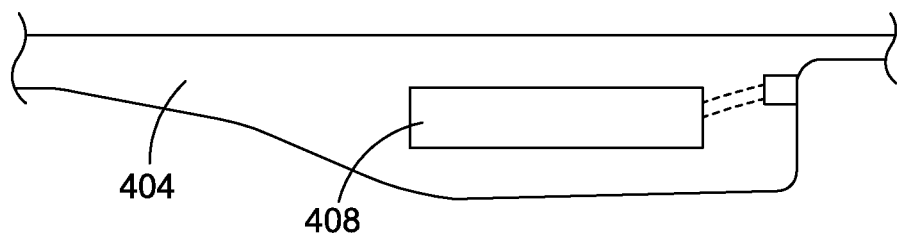
FIGS. 4A and 4B illustrate cross-sections of tubing having an example sensor disposed in the tubing wall according to an embodiment of the present invention.

Turning now to FIG. 4A, ° a cutaway view of placement of a pressure sensor 408 within an expanded portion of a tubing 404 is illustrated. In an example embodiment, the tubing 404 is configured with a first thickness for a portion of the length of the tubing 404. The tubing 404 is further configured with a second, larger thickness for another portion of the length of the tubing 404. The pressure sensor 408 is disposed within the thicker portion of the tubing 404, for example, in a "pocket" or other recess or cavity at least partially defined by the tubing 404. Moreover, the pressure sensor 408 may be molded into the tubing 404 upon manufacture of the tubing 404. The pressure sensor 408 may also be placed within a void, recess, pocket, or other available space at least partially defined by the tubing 404 subsequent to manufacture of the tubing 404.

Figure 4B:
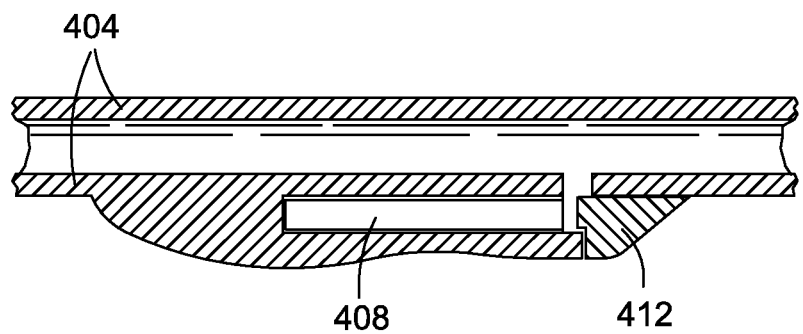

In an example embodiment illustrated in FIG. 4B, the pressure sensor 408 may be retained in the wall of the tubing 404 in connection with the use of a plug 412. The plug 412 may be made of the same material as the tubing 404. The plug 412 may also be made of a different material than the tubing 404, for example, an incompressible material configured to frictionally couple to the material of the tubing 404. The plug 412 may be at least partially inserted into and/or wedged between portions of the tubing 404. In this manner, the pressure sensor 408 may be retained in a portion of the tubing 404. The plug 412 may be removed as desired, for example, in order to replace a non-functioning pressure sensor 408, or to upgrade the pressure sensor 408 to a new pressure sensor 408 having expanded functionality, extended communication range, or other desirable properties.

Figure 4C:
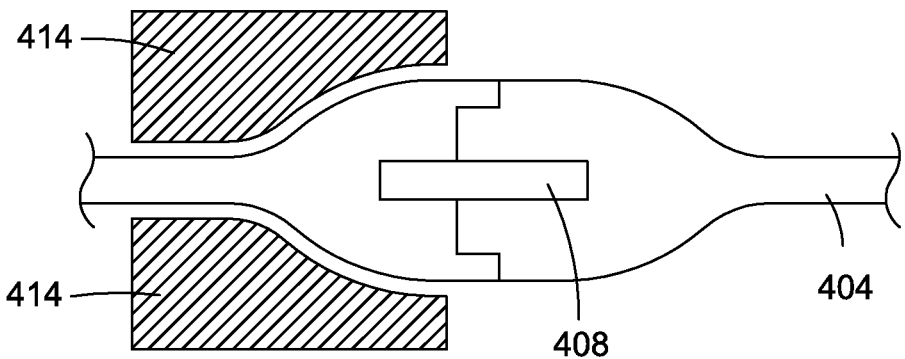
FIG. 4C illustrates an example configuration of components including a hard connector and stress relief components according to an embodiment of the present invention.

In another example embodiment illustrated in FIG. 4C, the pressure sensor 408 may be coupled to the tubing 404 at a joint, for example, a joint associated with a hard connector 414. As illustrated, multiple portions of the tubing 404 are each configured with a wider portion having, for example, complementary cavities therein. The pressure sensor 408 is disposed within the complementary cavities of the tubing 404, and the ends of the tubing 404 are then brought together, such that the pressure sensor 408 is surrounded by the tubing 404. One or more hard connector components 414 may similarly be coupled together, securing the pressure sensor 408 within the tubing 404. Additionally, the expanded thickness of the tubing 404 near the hard connector 414 can confer additional stress relief to the tubing 404.

Figure 5A:
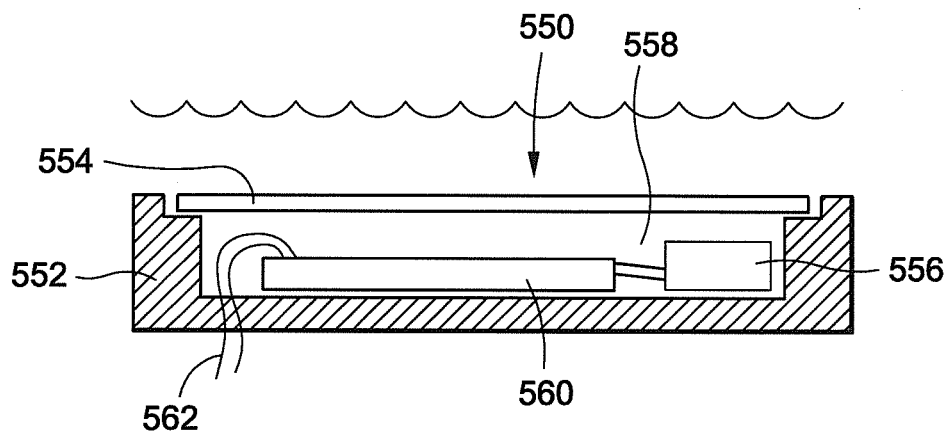
FIGS. 5A and 5B illustrate cross-sections of an example pressure sensor according to an embodiment of the present invention.
Figure 5B:
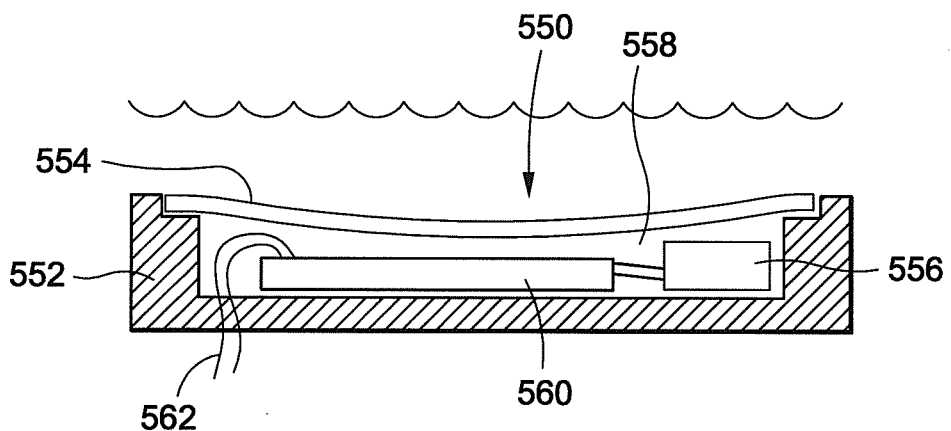

FIGS. 5A and 5B illustrate configuration and operation of an exemplary pressure sensor according to an embodiment of the present invention. Referring to FIG. 5A, in an example embodiment, a pressure sensor 550 is hermetically sealed and comprises a housing 552, for example, a metallic housing, and a membrane 554, both of which may comprise titanium or other non-radioopaque material. The membrane 554 flexes in response to changes in pressure, which affects the pressure transducer 556. Space inside the housing 552 may contain a pressure transfer medium 558, for example, degassed silicone oil or other suitable incompressible pressure transfer medium. The pressure transfer medium 558 may at least partially surround and/or immerse various components within the housing 552, for example, the pressure transducer 556, a microcontroller 560 coupled to the pressure transducer 556, a signal wire 562, and/or the like. In an example embodiment, the surface area of membrane 554 is large in comparison to the volume of the pressure transfer medium occupying the interior of the housing 552.

As pressure outside the pressure sensor 550 is increased, as illustrated in FIG. 5B, the membrane 554 deflects downward increasing the pressure of the pressure transfer medium 558. Similarly, as pressure outside the pressure sensor 550 is decreased, the membrane 554 deflects a reduced amount, reducing the pressure on the pressure transfer medium 558. The pressure transducer 556 converts pressure changes into changes in a suitable electromagnetic property, for example, capacitance, inductance, resistance, and/or the like. The changes in the electromagnetic property are proportional to the changed in the measured pressure. The changes in the electromagnetic property are then detected by the microcontroller 560, for example, via periodic and/or continuous polling or other querying of the pressure transducer 556 by the microcontroller 560. The microcontroller 560 converts the signal from the pressure transducer 556, which may be an analog signal susceptible to noise, interference, and/or the like, into a suitable signal, for example, an analog or digital signal having a suitable signal to noise ratio, configured to be delivered to a remote location. In one example, a signal from the microcontroller 560 passes through the housing 552 via the signal wire 562 which may be configured to be substantially immune to typical levels of electrical noise. In another example, a signal from the microcontroller 560 may be wirelessly transmitted beyond the confines of the pressure sensor 550, for example, by an antenna or other components integrated with and/or coupled to the microcontroller 560.

The pressure sensor 550 may further comprise various components, for example, antennas, capacitors, inductors, transistors, electrical couplings, connectors, and/or the like, configured to permit the pressure sensor 550 to communicate with and/or receive operating power from a remote control, for example, remote controller unit 110. Such components may be located on and/or may comprise part of a microcontroller 560. Such components may also be coupled to the microcontroller 560 inside the housing 552. Such components may also be located on the outside of the housing 552, for example in order to facilitate wireless communication with the remote controller unit 110, or to facilitate wired and/or wireless communication with other components of a gastric banding system (e.g., other sensors, an access port, a pump, and/or the like).

Figure 5C:
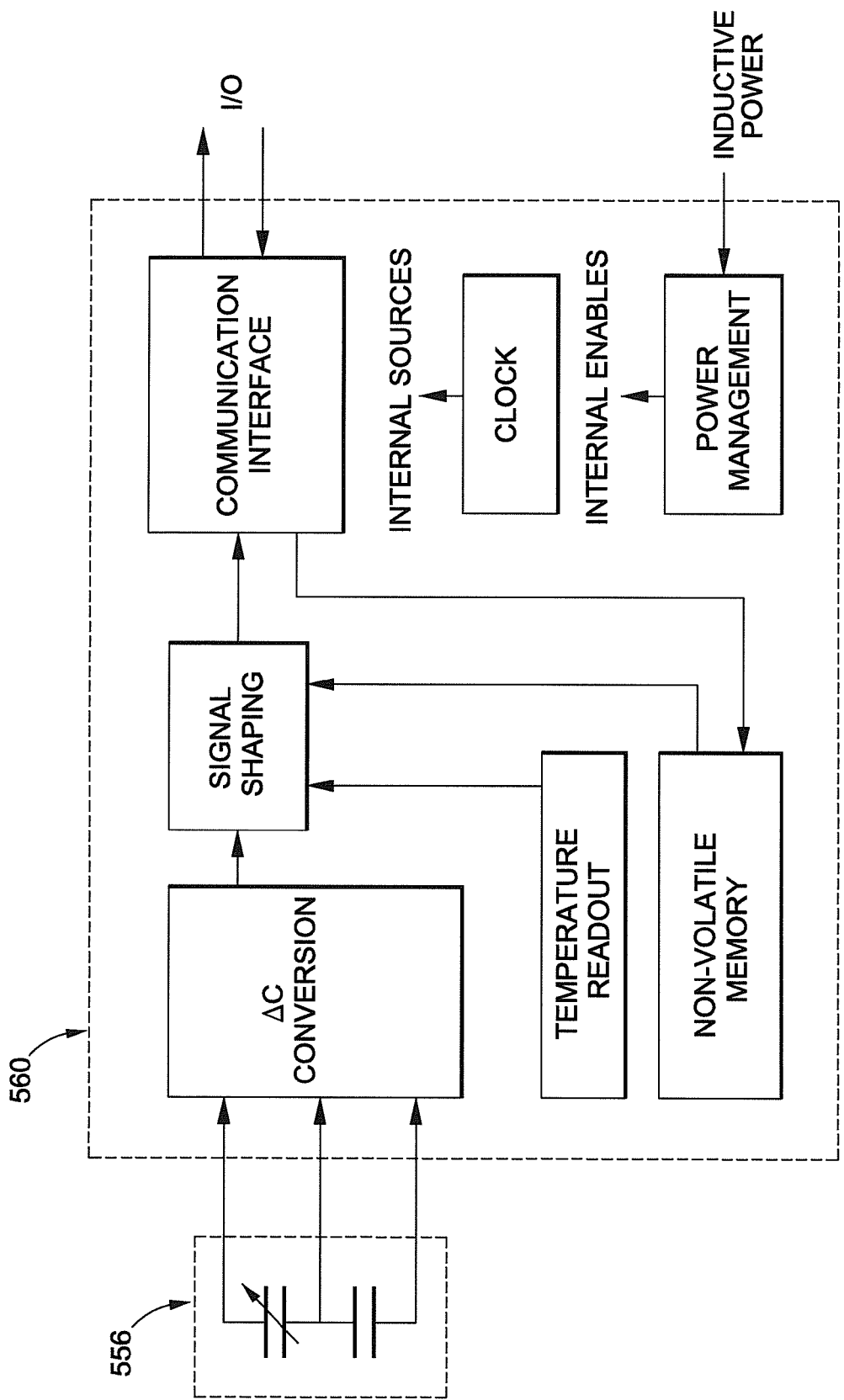
FIG. 5C illustrates example components of a microcontroller and a pressure transducer according to an embodiment of the present invention.

With additional reference now to FIG. 5C, in an example embodiment the microcontroller 560 comprises an application specific integrated circuit (ASIC) having various memories, signal processors, communications components, power components, temperature sensors, and/or the like. The microcontroller 560 is configured to manage and/or condition incoming electrical power received from the remote controller unit 110, for example via inductive coupling. The microcontroller 560 is further configured to utilize an internal temperature sensor to obtain temperature information. Responsive to temperature information, the microcontroller 560 may perform temperature compensation in order to adjust for changes in the behavior of one or more components of the pressure sensor 550.

In various example embodiments, the microcontroller 560 stores calibration values associated with one or more components of the pressure sensor 550 in on-board memory on the microcontroller 560. For example, one or more calibration values may be stored on the microcontroller 560 in order to correct for non-linear behavior and/or offsets associated with one or more components of the pressure sensor 550, for example the pressure transducer 556. The calibration values may be revised and/or updated, as suitable, in order to allow the pressure sensor 550 to report an accurate pressure reading to the remote controller unit 110. Additionally, the microcontroller 560 may format pressure data, temperature data, and/or other data for transmission to the remote controller unit 110. Moreover, the microcontroller 560 may be configured to respond as a slave to a master unit, for example another microcontroller 560 in another pressure sensor 550, a microprocessor in the remote controller unit 110, and/or the like.

In an example embodiment, the microcontroller 560 comprises an ASIC having a form factor of about 1.5 mm by 3.15 mm by 0.2 mm. In other example embodiments, the microcontroller may have a larger and/or smaller form factor, in order to allow the microcontroller 560 to be placed within the pressure sensor 550 and/or immersed in the pressure transfer medium 558 therein.

The pressure sensor 550 is configured to withstand high temperatures, for example, temperatures in excess of temperatures necessary for steam sterilization (e.g., temperatures in excess of 120 degrees Celsius), without damage to the pressure transducer 556 or other components of the pressure sensor 550 caused by expansion of the pressure transfer medium 558. Notably, the pressure sensor 550 achieves this result without resorting to fillers intended to lower the overall thermal expansion coefficient of the pressure transfer medium 558, for example, fillers comprising glass beads, metal fragments, and/or the like, as such fillers can lead to undesirable increases in manufacturing complexity and/or cost. Additionally, the pressure sensor 550 minimizes the internal volume which is filled with the pressure transfer medium 558 while maximizing the surface area of the membrane 554. This design minimizes the stress on the membrane for a given increase in the temperature of the sensor 550. Moreover, because the pressure sensor 550 receives operational power from the remote controller unit 110, no battery or other implanted power source is required for operation of the pressure sensor 550.

The pressure sensor 550 in accordance with various exemplary embodiments may comprise a pressure sensor, multiple pressure sensors, including multiple pressure sensors configured to operate in a differential mode, a flow rate sensor, and/or the like or combinations thereof.

Returning again to FIG. 1B, the gastric banding system 100B may comprise a plurality of the pressure sensors 108 disposed, for example, within the tubing 104. In an exemplary embodiment, two pressure sensors 108 are situated within the high precision pump unit 114. During a filling or draining condition, as well as during a no-flow condition, both of the pressure sensors 108 may be used to measure pressure, thereby providing the benefits of redundancy and averaging. Moreover, any suitable number of the pressure sensors 108 may be utilized.

The systems and apparatus described herein further include the remote controller unit 110 (not shown), which provides access to system data and functions. The remote controller unit 110 may be an external, handheld, reusable battery-powered device, or any other suitable electronic device. The remote controller unit 110 can be made of any rugged material, including polypropylene, cyclicolefin co-polymer, nylon, and other compatible polymers and the like. The remote controller unit 110 is not implanted within the patient, so hermetic sealing of the unit is not required. However, the remote controller unit 110 is preferably at least water resistant, if not waterproof, and may be cleaned using standard hospital disinfectants without damage to the unit.

Further, the remote controller unit 110 is configured with a user interface including at least one display and at least one user input. In some example embodiments, the display and the user input are combined in the form of a touch screen with a color display. In other embodiments, the display is grayscale. The remote controller unit 110 permits a clinician or a patient to interact with the gastric banding system 100B, for example, by navigating through menu driven screens used for data entry, data collection, and control of other components of the gastric banding system 100B.

The remote controller unit 110 is capable of communicating with the pressure sensor 108, the high precision pump unit 114, and/or other components of a gastric banding system, for example, the gastric banding system 100B. "Capable of communicating" as used herein refers to the ability of the remote controller unit 110 to establish communications with other components, yet still have the ability to break communication and the systems described herein still function. To establish communication, in one example embodiment, once the remote controller unit 110 is initialized, a display shows a searching query for nearby compatible components, for example, the high precision pump unit 114, the pressure sensor 108, and/or the like. As the remote controller unit 110 is brought into range of a compatible component, a symbol displays the strength of the communication link. Once stable communications have been acquired, the display may show the serial number or other identifying indicia of the component or system so a clinician can verify they have the appropriate patient records in hand.

Via the remote controller unit 110, the clinician can obtain information from and/or issue commands to other components of the gastric banding system. For example, if the patient requires a tightening of the gastric band 106, the clinician can enter the amount of the desired volume increase. If the patient requires a loosening of the gastric band 106, the clinician can enter the amount of the desired volume decrease. Current and/or logged pressure readings from the pressure sensor 108 may similarly be obtained. The remote controller unit 110 can also display the current and/or desired volume within the gastric band 106 and indicate the new volume as the gastric band 106 fills or drains.

To verify an appropriate adjustment has been made to the system, the clinician can set the remote controller unit 110 into a pressure monitor mode and request that the patient drink water. The display may show a real time graph of one or more pressure readings measured within the gastric banding system 100B, for example, by one or more of the pressure sensors 108. This diagnostic tool may show higher pressures and warning messages if the gastric band 106 has been overtightened.

The remote controller unit 110 can synchronize and charge when coupled with a charging cradle or docking station. This docking station provides the ability to recharge a battery for the remote controller unit 110, and may also provide a link to download information to a personal computer such as the adjustment history of a patient. Other data that can be stored on the remote controller unit 110 and downloaded from the high precision pump unit 114 and/or the pressure sensor 108 includes, but is not limited to, serial number, gastric band size, patient information, gastric band volume, current pressure, historical pressure, firmware version and patient adjustment history. This data can be downloaded directly to a patient tracking database for ease of tracking.

Any data stored on the remote controller unit 110, on the pressure sensor 108, and/or on the high precision pump unit 114 can be electronically secured. In other words, security measures can be put in place to keep the data confidential, including communication between the high precision pump unit 114 and the remote controller unit 110, communication between the high precision pump unit 114 and the pressure sensor 108, and/or other communications between various components of the gastric banding system 100B. Security measures can include computer generated algorithms that prevent intrusion by outside parties.

In an example embodiment, the pressure sensor 108 is a passive device configured to be powered by and/or communicate with the remote controller unit 110 when it is in close proximity. For example, in one example embodiment, the remote controller unit 110 may be configured to power and communicate with the pressure sensor 108 at a distance less than about 8 inches, preferably less than about 4 inches (about 10.2 cm) of tissue plus about 4 inches, preferably about 2 inches (about 5.1 cm) of air. Moreover, power and communications can be tailored to transmit over longer distances, or can be tailored to have the remote controller unit 110 placed on the skin adjacent to the pressure sensor 108.

The remote controller unit 110 can inductively power and telemetrically control the pressure sensor 108. The remote controller unit 110 may be configured to provide continuous power to the pressure sensor 108. In an example embodiment, a dedicated microcontroller within the remote controller unit 110 monitors the amount of power that is transmitted. Further, a power management system may be implemented to optimize energy transmission between the remote controller unit 110 and the pressure sensor 108 relative to their separation distance. For example, the power transmission may automatically decrease as the remote controller unit 110 is moved closer to the pressure sensor 108, and may be increased as the distance is increased. This reduces wasted energy, and energy exposure to the patient.

Returning to FIGS. 5A and 5B, in an example embodiment, the pressure sensor 550 is a passive device which may be entirely controlled and powered by the remote controller unit 110. An antenna on the microcontroller 560 housed within the pressure sensor 550 couples to the remote controller unit 110 to allow the transmission of power through the skin and/or subcutaneous tissue. In another embodiment, the antenna providing power is located outside of the pressure sensor 550. The power issued from the remote controller unit 110 may be continually monitored by a dedicated microprocessor to ensure that power transmission is suitably reduced and/or minimized to the lowest level required for operation. To reduce the power transmission and to improve command communication, the pressure sensor 108 and the remote controller unit 110 may have a channel frequency dedicated to command communication and a separate channel frequency dedicated to power transmission. The command communication can be configured, for example, to take place at about 402-406 MHz while the power transmission, for example, takes place at about 400 kHz. This command communication adheres to the frequency and power standards set by the Medical Implant Communications Service. Other communication and/or power frequency ranges may be utilized, as desired. To ensure accuracy, communication and control commands may be verified prior to data reporting or command implementation, for example, by error checking and/or correction algorithms.

The systems and apparatus described herein use common surgical techniques to place the components in their respective positions within a patient. The surgical techniques may be identical or similar to those used in the placement of conventional gastric banding systems. For example, the gastric band 106 may be placed around the stomach using laparoscopic techniques, as known to those of skill in the art. Like a conventional access port, the high precision pump unit 114 and/or the access port 102 may be sutured onto the rectus muscle sheath or any other conveniently accessible muscle. For example, in order to achieve a secure attachment of the high precision pump unit 114, it may be sutured to the rectus muscle and remain securely attached for forces below about 6 pound-force (about 26.6 Newtons), and preferably below about 3 pound-force (about 13.3 Newtons). The tubing 104 passes through the rectus muscle into the peritoneal cavity.

The systems and apparatus of the present invention further allow for remotely monitored pressure and controlled adjustment without needles, non-invasively, by using the remote controller unit 110. Also, should the remote controller unit 110 be unavailable, damaged, out of power, or in the event of an emergency, an adjustment of the gastric band 106 can be performed invasively using a needle. For example, by using the access port 102 illustrated in FIGS. 1A and 1B, a clinician can choose to use a standard needle for adjustments. If any of the electronics associated with the systems and apparatus described herein become inoperable, the access port 102 can be used to add or remove the fluid from the gastric band 106. The access port 102 and a syringe or needle can be used to adjust the gastric band 106.

The systems described herein generally function as follows. A clinician uses the remote controller unit 110 to query one or more of the pressure sensors 108. The pressure sensors 108 are activated responsive to an energy pulse from the remote controller unit 110. The pressure sensors 108 may then take pressure readings, store pressure values or other information, and/or transmit current and/or historical pressure values or other information to the remote controller unit 110. Updated configuration information, command information, control information, diagnostic information, reset information, and/or other suitable information may be sent to and/or from the remote controller unit 110 and the pressure sensor 108. Responsive to information from the pressure sensor 108 and/or other suitable information or operating parameters, the remote controller unit 110 may subsequently and/or simultaneously communicate with and/or power the high precision pump unit 114 in order to adjust the gastric band 106. In an example embodiment, the remote controller unit 110 communicates simultaneously with the pressure sensor 108 and the high precision pump unit 114 in order to monitor pressure changes in the gastric banding system during filling and/or draining of the gastric band 106. In one example, the total power consumed by the pressure sensor 108, the high precision pump unit 114, and all other inductively powered components of gastric banding system 100B during simultaneous operation thereof is less than 1 watt. In another example, the total power consumed is less than 700 milliwatts.

As described herein, the present systems and apparatus may be compatible with magnetic resonance imaging (MRI), which is much safer for a patient than exposure to X-ray radiation. In one example embodiment, the systems and apparatus described herein are configured and structured to be compatible with MRI, or MRI safe, at magnetic field strengths of up to about 1.5 Tesla. For example, the pressure sensor 108 may be entirely inductively powered. The pressure sensor 108 may utilize no permanent magnets, no long metallic wires or leads, and a minimal or negligible amount of ferrous or ferromagnetic material. The pressure sensor 108 may be substantially free of or contain substantially no ferromagnetic materials. Substantially no ferromagnetic materials refers to materials containing less than about 5%, preferably less than about 1% or 0.1% (w/w) of ferromagnetic material. The resulting systems are thus MRI safe given standard specifications regulating translational and rotational attraction, MRI heating, and imaging artifacts. All materials selected for the systems are preferably selected to be compatible and safe in an MRI environment.

Further, the inductive powering of the pressure sensor 108 utilizes energy passed through the body tissue. Since the body tissue absorbs a portion of the energy passing through it, the heating of the body tissue can be proportional to the total energy transferred. To ensure that the systems meet standards to minimize tissue heating (below 2° C. above body temperature per ISO 45502), the pressure sensors 108 described herein have been designed to use very little power to measure pressure within the system, for example, less than about 2 milliwatts, or preferably less than about 1.35 milliwatts, and do not cause excessive heating of the patient's body tissue.

Using the remote controller unit 110 to communicate with the pressure sensor 108, a clinician can monitor pressure inside the gastric band 106, for example, in "real time" during an adjustment of the constriction within the gastric band 106. This allows the clinician to observe the response of the gastric band 106 to a patient's adjustment. A new modality for gastric band adjustment management is thus enabled, because clinicians can monitor static pressure, as well as pressure and volumes during adjustments. With these pressure sensing capabilities, the clinician can make expanded determinations, for example, whether there is a leak within the system (e.g., an unexpectedly low, declining, or zero pressure reading), or whether there is an obstruction in the system (e.g., an unexpectedly high pressure reading or prolonged pressure rise).

In one example embodiment of the present invention, components of the systems can be replaced without replacing the entire system and subjecting patients to overly invasive surgeries to replace entire systems when a single component is defective or damaged. For example, if the pressure sensor 108 becomes damaged, unreliable, or inoperable, it can be replaced independently of other components. Additionally, if multiple pressure sensors 108 are used, the system can continue to operate with a reduced number of operational pressure sensors 108 should one or more of the pressure sensors 108 fail.

The systems described herein are configured to meet at least one safety specification. For example, in the event of any failure of the systems, either no change in the gastric band 106 tightness or a loosening of the gastric band 106 results. Further, the high precision pump unit 114 and the pressure sensor 108 are biocompatible for long term implantation, and the remote controller unit 110 is biocompatible for transient use both per ISO 10993. The systems are designed to have no significant interaction or interference with other electronics in any of the following modalities: implantable energy sources such as defibrillators and pacemakers; internal energy sources such as electrosurgical instruments; external energy sources such as ultrasound, x-rays and defibrillators; and radiofrequency signals such as pacemaker programmers and neuron-stimulators.

Sensing or measuring the pressure within a gastric banding system, for example within the fluid pathway of the gastric banding system 100B, provides diagnostic uses. Clinicians can measure pressure while a patient drinks water, recording and analyzing resulting pressure fluctuations which can help determine if the gastric band 106 is too restrictive. A band that is too restrictive can also be confirmed by the patient's response (generally discomfort) upon drinking the water, and can then be appropriately adjusted. Further, sensing or measuring pressure in the gastric banding system 100B can be useful in diagnosing system leaks or obstructions. For example, if the pressure consistently drops over an extended period of time, the clinician can diagnose a leak within the system and plan for an appropriate treatment to fix the problem. In contrast, if there is an obstruction within the system with a sustained pressure rise over time, the clinician can diagnose an obstruction within the system and plan for an appropriate treatment to fix the problem.

The pressure sensor 108 may be utilized on a short term basis and/or a long term basis. For example, the pressure sensor 108 may be utilized during the course of a patient visit with a clinician, which may be anywhere from a few minutes to several hours in duration. Information from the pressure sensor 108 may be used to analyze changes in pressure which occur during various intentional patient actions, for example, swallowing. Information from the pressure sensor 108 may also be used to detect unintentional patient actions, for example, smooth muscle fasciculations, reflexive actions, spasming, cramping, and/or the like.

On a longer term basis, the pressure sensor 108 may also be used, for example, to compare pressure readings from one clinical visit to the next, from one year to the next, and/so on. Long-term changes in pressure reported by the pressure sensor 108 may be utilized to detect system leaks, capsular contraction around the stomach, herniation and/or erosions within the stomach, and/or the like. In this manner, the pressure sensor 108 can provide additional information to enable the clinician to determine a suitable course of care for the patient.

Moreover, the pressure sensor 108 may also be retrofitted to an existing gastric banding system. For example, an existing gastric banding system may be configured with tubing lacking a pressure sensor 108. A minor surgical procedure may replace at least a portion of the existing tubing with the new tubing 104 having one or more pressure sensors 108 therein. Thus, pressure monitoring capabilities can be extended to existing patients without requiring removal and/or replacement of various existing components of their gastric banding systems, for example access ports, gastric bands, pumps, batteries, valves, and/or the like.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the present invention.

Groupings of alternative elements or embodiments of the present invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the present invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

In closing, it is to be understood that the embodiments of the present invention disclosed herein are illustrative of the principles of the present invention. Other modifications that may be employed are within the scope of the present invention. Thus, by way of example, but not of limitation, alternative configurations of the present invention may be utilized in accordance with the teachings herein. Accordingly, the present invention is not limited to that precisely as shown and described.

What is claimed is:

1. An implantable system that monitors static and fluctuating pressure levels of a fluid moving to and from an inflatable portion of a gastric band, the implantable system comprising:
a first pressure sensor including,
    a housing defining a cavity and having an open top portion,
    a flexible membrane covering the open top portion of the housing and having an inner surface facing the cavity and an outer surface capable of contacting the fluid,
    a pressure transfer fluid located within the cavity,
    a sensing element, entirely positioned within the cavity of the housing and positioned adjacent to the flexible membrane, for measuring a pressure on the flexible membrane, the pressure being caused by the fluid contacting the outer surface of the flexible membrane, for converting the pressure to a pressure signal, and
    a microcontroller positioned within the cavity of the housing and coupled to the sensing element, the microcontroller configured to process the pressure signal received from the sensing element and transmit the processed pressure signal to a location external to the implantable system; and
a second pressure sensor including,
    a housing defining a cavity and having an open top portion,
    a flexible membrane covering the open top portion of the housing and having an inner surface facing the cavity and an outer surface capable of contacting the fluid,
    a pressure transfer fluid located within the cavity,
    a sensing element, entirely positioned within the cavity of the housing and positioned adjacent to the flexible membrane, for measuring a pressure on the flexible membrane, the pressure being caused by the fluid contacting the outer surface of the flexible membrane, for converting the pressure to a pressure signal, and
    a microcontroller positioned within the cavity of the housing and coupled to the sensing element, the microcontroller configured to process the pressure signal received from the sensing element and transmit the processed pressure signal to a location external to the implantable system,
    wherein the implantable system is located within a wall of a tubing through which the fluid moves to and from the inflatable portion of the gastric band,
wherein the first and second pressure sensors monitor static and fluctuating pressure levels of a fluid moving to and from the inflatable portion of the gastric band by operating in a differential mode.

2. The implantable system of claim 1, wherein the pressure transfer fluid is degassed silicone oil.

3. The implantable system of claim 1, wherein, for each of the first and second pressure sensors, the respective flexible membrane moves toward the respective sensing element when the fluid applies pressure to the respective outer surface of the flexible membrane.

4. The implantable system of claim 1, further comprising a remote device, wherein the remote device is configured to receive the pressure signal transmitted by the microcontroller of the first pressure sensor and the pressure signal transmitted by the microcontroller of the second pressure sensor, and wherein the remote device wirelessly provides power for operation of the implantable system.

5. The implantable system of claim 4, wherein the remote device receives the pressure signal transmitted by the microcontroller of the first pressure sensor and the pressure signal transmitted by the microcontroller of the second pressure sensor and displays the pressure signal transmitted by the microcontroller of the first pressure sensor and the pressure signal transmitted by the microcontroller of the second pressure sensor on a display component of the remote device.

6. The implantable system of claim 1, wherein for each of the first and second pressure sensors the pressure on the respective flexible membrane changes an electrical property of the respective sensing element.

7. The implantable system of claim 6, wherein the electrical property is detected by periodic or continuous polling of the respective sensing element by the respective microcontroller.

8. The implantable system of claim 1, wherein the first and second pressure sensors are disposed in a lumen in fluid communication with the inflatable portion, and wherein the lumen comprises a plurality of extensions constructed to pass the fluid by the first and second pressure sensors.

9. The system of claim 8, wherein the lumen is disposed within tubing, and wherein the plurality of extensions allow the fluid to pass by the first and second pressure sensors when the tubing is kinked.

10. The implantable system of claim 1, wherein for each of the first and second pressure sensors, at least one of the respective sensing element and the respective microcontroller are at least partially immersed in the respective pressure transfer fluid.

11. The implantable system of claim 1, wherein for each of the first and second pressure sensors, the respective pressure signal is based in part on the pressure of the respective pressure transfer fluid caused by the fluid contacting the respective outer surface of the respective flexible membrane.

12. The implantable system according to claim 1, wherein at least one of the sensing elements and the microcontrollers are at least partially immersed in their respective pressure transfer fluid.

13. In a gastric banding system having tubing carrying fluid moving to and from an inflatable portion of a gastric band, an implantable pressure sensor that monitors static and fluctuating pressure levels of the fluid, the sensor comprising:
    a housing defining a cavity and having an open top portion, the housing contained in at least a portion of the tubing;
    a flexible membrane covering the open top portion of the housing and having an inner surface facing the cavity and an outer surface capable of contacting the fluid;
    a pressure transfer fluid located within the cavity;
    a sensing element, entirely positioned within the cavity of the housing and positioned adjacent to the flexible membrane, for measuring a pressure on the flexible membrane, the pressure being caused by the fluid contacting the outer surface of the flexible membrane, for converting the pressure to a pressure signal; and
    a microcontroller positioned within the cavity of the housing and coupled to the sensing element, the microcontroller configured to process the pressure signal received from the sensing element and transmit the processed pressure signal to a location external to the implantable pressure sensor.

14. The sensor according to claim 13, wherein the housing is integrated into the tubing.

15. In a gastric banding system having tubing that defines a lumen carrying fluid moving to and from an inflatable portion of a gastric band, an implantable pressure sensor that monitors static and fluctuating pressure levels of the fluid, the sensor comprising:
- a housing defining a cavity and having an open top portion, the housing contained in the lumen of the tubing;
- a flexible membrane covering the open top portion of the housing and having an inner surface facing the cavity and an outer surface capable of contacting the fluid;
- a pressure transfer fluid located within the cavity;
- a sensing element, entirely positioned within the cavity of the housing and positioned adjacent to the flexible membrane, for measuring a pressure on the flexible membrane, the pressure being caused by the fluid contacting the outer surface of the flexible membrane, for converting the pressure to a pressure signal; and
- a microcontroller positioned within the cavity of the housing and coupled to the sensing element, the microcontroller configured to process the pressure signal received from the sensing element and transmit the processed pressure signal to a location external to the implantable pressure sensor.

* * * * *